United States Patent
Bellemere et al.

(10) Patent No.: US 12,061,189 B2
(45) Date of Patent: Aug. 13, 2024

(54) MODELS OF RECONSTRUCTED SENSITIVE SKIN

(71) Applicant: Laboratoires Expanscience, Paris la Defense (FR)

(72) Inventors: Gaelle Bellemere, Bihorel (FR); Stephanie Bredif, Croisilles (FR); Gaetan Boyer, Coulombs (FR); Caroline Baudouin, Rambouillet (FR)

(73) Assignee: Laboratoires Expanscience, Paris la Defense (FR)

( * ) Notice: Subject to any disclaimer, the term of this patent is extended or adjusted under 35 U.S.C. 154(b) by 599 days.

(21) Appl. No.: 16/624,087

(22) PCT Filed: Jun. 21, 2018

(86) PCT No.: PCT/EP2018/066542
§ 371 (c)(1),
(2) Date: Dec. 18, 2019

(87) PCT Pub. No.: WO2018/234430
PCT Pub. Date: Dec. 27, 2018

(65) Prior Publication Data
US 2020/0256853 A1 Aug. 13, 2020

(30) Foreign Application Priority Data
Jun. 22, 2017 (FR) ...................................... 1755697

(51) Int. Cl.
*G01N 33/50* (2006.01)
*C12N 5/071* (2010.01)

(52) U.S. Cl.
CPC ....... *G01N 33/5088* (2013.01); *C12N 5/0698* (2013.01); *C12N 2503/06* (2013.01)

(58) Field of Classification Search
CPC .............. G01N 33/5088; C12N 5/0698; C12N 2503/06
See application file for complete search history.

(56) References Cited

U.S. PATENT DOCUMENTS

| | | | |
|---|---|---|---|
| 4,849,077 A | 7/1989 | Rosenthal et al. | |
| 4,882,127 A | 11/1989 | Rosenthal et al. | |
| 6,723,513 B2 | 4/2004 | Lexow | |
| 7,556,922 B2 | 7/2009 | Block et al. | |
| 2006/0275782 A1 | 12/2006 | Gunderson et al. | |
| 2007/0148771 A1 | 6/2007 | Chopart et al. | |
| 2008/0020392 A1 | 1/2008 | Block et al. | |
| 2008/0138850 A1* | 6/2008 | Vielhaber et al. | C12Q 1/02 435/29 |
| 2009/0181385 A1 | 7/2009 | McKernan et al. | |
| 2009/0181860 A1 | 7/2009 | McKernan et al. | |
| 2009/0186349 A1 | 7/2009 | Gunderson et al. | |
| 2010/0099576 A1 | 4/2010 | Comer et al. | |

FOREIGN PATENT DOCUMENTS

| | | |
|---|---|---|
| EP | 29678 B1 | 5/1983 |
| EP | 0296078 A1 | 12/1988 |
| EP | 285471 B1 | 1/1991 |
| EP | 789074 B1 | 12/2003 |
| EP | 1451302 A1 | 9/2004 |
| EP | 1141399 B1 | 8/2005 |
| EP | 1878790 A1 | 1/2008 |
| EP | 1974718 A1 | 10/2008 |
| WO | 0191821 A1 | 12/2001 |
| WO | 0192322 A1 | 12/2001 |
| WO | 2002070729 A2 | 9/2002 |
| WO | 2003066896 A2 | 8/2003 |
| WO | 2006063864 A2 | 6/2006 |
| WO | 2006063865 A2 | 6/2006 |
| WO | 2006084132 A2 | 8/2006 |
| WO | 2007064305 A1 | 6/2007 |
| WO | 2007111924 A2 | 10/2007 |
| WO | 2008096868 A1 | 8/2008 |
| WO | 2014028734 A1 | 2/2014 |
| WO | 2015101677 A1 | 7/2015 |
| WO | 2015104413 A1 | 7/2015 |

OTHER PUBLICATIONS

Rendl et al., Topically applied lactic increases spontaneous secretion of vascular endothelial growth factor by human reconstructed epidermis, British Journal of Dermatology, 145: 3-9 (Year: 2001).*
Casas et al., In vitro human skin irritation test for evaluation of medical device extracts, Toxicology in Vitro, 27: 2175-2183. (Year: 2013).*
Nakamura et al., Full-thickness human skin explants for testing the toxicity of topically applied chemicals, The Society for Investigative Dermatology, 95: 325-332. (Year: 1990).*
Groeber et al., Skin tissue engineering—in vivo and in vitro applications, Advanced Drug Delivery Reviews, 128: 352-366. (Year: 2011).*
MatTek, In Vitro EpiDerm Skin Irritation Test (EPI-200-SIT) for use with MatTek's Reconstructed Human Epidermal Model EpiDerm (EPI-200-SIT). (Year: 2022).*
Castex-Rizzi et al., "In vitro approaches to pharmacological screening in the filed of atopic dermatitis," British Journal of Dermatology, vol. 170, pp. 12-18, Jul. 2014.
Hernandez-Pigeon et al., "A new model of "fragile skin" in vitro on human keratinocytes and reconstructed epidermis", The Journal of Investigative Dermatology: Official Journal of the Society for Investigative Dermatology and the European Society for Dermatological Research, May 2014, vol. 134(Supp. 1) Abstract 370, p. S64, Elsevier.

(Continued)

*Primary Examiner* — Laura Schuberg
*Assistant Examiner* — Joseph Paul Miano
(74) *Attorney, Agent, or Firm* — Rouget F. Henschel; Potomac Law Group, PLLC

(57) ABSTRACT

The present invention relates to models of reconstructed sensitive skin reproducing the features of sensitive skin, as well as to processes for obtaining such models. The present invention further relates to in vitro processes for testing formulations or active ingredients for the prevention or treatment of sensitive skin.

7 Claims, 2 Drawing Sheets

(56) References Cited

OTHER PUBLICATIONS

Figure 1:
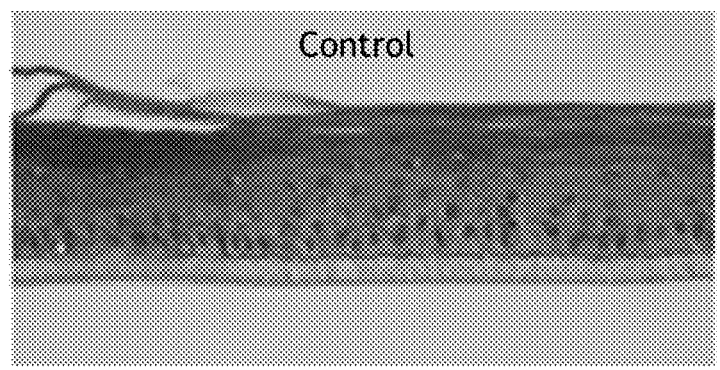
Figure 1:
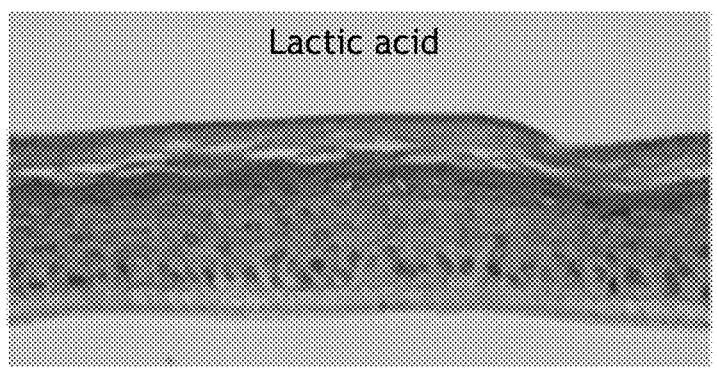

International Search Report dated Sep. 11, 2018 issued in International Application No. PCT/EP2018/066542.
Netzlaff et al.,, "The human epidermis models EpiSkin(R), SkinEthic(R) and EpiDerm(R): An evaluation of morphology and their suitability for testing phototoxicity, irritancy, corrosivity, and substance transport", European Journal of Pharmaceutics and Biopharmaceutics, Mar. 2005, vol. 60(2), pp. 167-178, Elsevier.
Poumay et al., "A simple reconstructed human epidermis: preparation of the culture model and utilization in in vitro studies," Arch. Dermatol. Res., vol. 296, pp. 203-211, 2004.
Wufuer, et al., "Skin-on-a-chip model simulating inflammation, edema and drug-based treatment", Scientific Reports, Nov. 2016, vol. 6(1), pp. 1-12, Nature Publishing.
Torres et al., "Study of the analysis of alkoxyglycerols and other non-polar lipids by liquid chromatography coupled with evaporative light scattering detector," Journal of Chromatography A, vol. 1078, pp. 28-34, 2005.
Vahlquist, "Markers of Skin Inflammation and Wound Healing," Acta Derm. Venereol., vol. 80, p. 161, 2000.
Van Smeden et al., "LC/MS analysis of stratum corneum lipids: ceramide profiling and discovery," Journal of Lipid Research, vol. 52, pp. 1211-1221, 2011.
Vrana et al., "Development of a Reconstructed Cornea from Collagen-Chondroitin Sulfate Foams and Human Cell Cultures," Vis. Sci., vol. 49, No. 12, pp. 5325-5331, 2008.
Vyumvuhore et al., "Raman spectroscopy: in vivo quick response code of skin physiological status," Journal of Biomedical Optics, vol. 19, No. 11, p. 111603, Nov. 2014.
Auxenfans et al., "Adipose-derived stem cells (ASCs) as a source of endothelial cells in the reconstruction of endothelialized skin equivalents," Journal of Tissue Engineering and Regenerative Medicine, vol. 6, pp. 512-518, Jul. 2011.
Auxenfans et al., "Evolution of three dimensional skin equivalent models reconstructed in vitro by tissue engineering," Eur. J. Dermatol., vol. 19, No. 2, pp. 107-113, Mar./Apr. 2009.
Bechetoille et al., "Effects of Solar Ultraviolet Radiation on Engineered Human Skin Equivalent Containing Both Langerhans Cells and Dermal Dendritic Cells," Tissue Engineering, vol. 13, No. 11, pp. 2667-2679, 2007.
Berardesca et al., "Sensitive skin: an overview," International Journal of Cosmetic Science, vol. 35, pp. 2-8, 2013.
Black et al., "Optimization and Characterization of an Engineered Human Skin Equivalent," Tissue Engineering, vol. 11, No. 5/6, pp. 723-733, 2005.
Bouwstra et al., "Structural Investigations of Human Stratum Corneum by Small-Angle X-Ray Scattering," The Journal of Investigative Dermatology, vol. 97, No. 6, pp. 1005-1012, Dec. 1991.
Caspers et al., "In Vivo Confocal Raman Microspectroscopy of the Skin: Noninvasive Determination of Molecular Concentration Profiles," The Journal of Investigative Dermatology, vol. 116, No. 3, pp. 434-442, Mar. 2001.
Castro-Perez et al., "Identifying Static and Kinetic Lipid Phenotypes by High Resolution UPLCMS: Unraveling Diet-Induced Changes in Lipid Homeostasis by Coupling Metabolomics and Fluxomics," Journal of Proteome, vol. 10, pp. 4281-4290, Jul. 2011.
Costin et al., "Vaginal Irritation Models: The Current Status of Available Alternative and in Vitro Tests," ATLA, vol. 39, pp. 317-337, 2011.
Daehnhardt-Pfeiffer et al., "Noninvasive Stratum Corneum Sampling and Electron Microscopical Examination of Skin Barrier Integrity: Pilot Study with a TopicalGlycerin Formulation for Atopic Dermatitis," Skin Pharmacology and Physiology, vol. 25, pp. 155-161, Mar. 2012.
Dayan et al., "Stratum Corneum: The Role of Lipids and Ceramides," Cosmetics & Toiletries, vol. 121, No. 1, pp. 37-44, 2006.
Dongari-Bagtzoglou et al., "Development of a highly reproducible three-dimensional organotypic model of the oral mucosa," Nat. Protoc., vol. 1, No. 4, pp. 2012-2018, 2006.

Downing et al., "Estimation of Sebum Production Rates in Man by Measurement of the Squalene Content of Skin Biopsies," The Journal of Investigative Dermatology, vol. 77, pp. 358-360, 1981.
Falcone et al., "Micropsectroscopic Confocal Raman and Macroscopic Biophysical Measurements in the in vivo Assessment of the Skin Barrier: Perspective for Dermatology and Cosmetic Sciences," Skin Pharmacol. Physiol., vol. 28, pp. 307-317, Sep. 2015.
Farwick et al., "Developments in Ceramide Identification, Synthesis, Function and Nomenclature," Cosmetics & Toiletries, vol. 124, vol. 2, pp. 63-72, Feb. 2009.
Fluhr et al., "Functional skin adaption in infacy—almost complete but not fully competent," Experimental Dermatology, vol. 19, No. 6, pp. 483-492, 2010.
Fuller et al., "The challenges of sequencing by synthesis," Nature Biotechnology, vol. 27, No. 11, pp. 1013-1023, 2009.
Gorcea et al., "Fourier transform infrared spectroscopy studies of lipid domain formation in normal and ceramide deficient stratum corneum lipid models," International Journal of Pharmaceutics, vol. 435, pp. 63-68, Nov. 2011.
Guenou et al., "Human embryonic stem cells derivative enable full reconstruction of the pluristratified epidermis," Lancet, vol. 374, No. 9703, pp. 1745-1753, 2009.
Henriksen et al., "The Relative Influences of Acidity and Polarity on Responsiveness of Small Organic Molecules to Analysis with Negative Ion Electrospray IonizationMass Spectrometry (ESI-MS)," J. Am. Soc. Mass Spectrom., vol. 16, pp. 446-455, 2004.
Hogan et al., "Skin Barrier Function and Its Importance at the Start of Atopic March," Journal of Allergy, vol. 2012, Article ID 901940, 2012.
Iwai et al., "The Human Skin Barrier Is Organized as Stacked Bilayers of Fully Extended Ceramides with Cholesterol Molecules Associated with the Ceramide Sphingoid Moiety," Journal of Investigative Dermatology, pp. 1-11, Apr. 2012.
Jungersted et al., "Lipids and skin barrier function—a clinical perspective," Contact Dermatitis, vol. 58, pp. 255-262, 2008.
Kinicoglu et al., "Reconstruction of a full-thickness collagen-based human oral mucosal equivalent," Biomaterials, vol. 30, pp. 6418-6425, Aug. 2009.
Kinikoglu et al., "The influence of elastin-like recombinant polymer on the self-renewing potential of a 3D tissue equivalent derived from human lamina propria fibroblasts and oral epithelial cells," Biomaterials, vol. 32, pp. 5756-5764, May 2011.
Kraehenbuehl et al., "Three-dimensional biomaterials for the study of human pluripotent stem cells," Nature Methods, vol. 8, pp. 731-736, Aug. 2011.
Lequeux et al., "A Simple Way to Reconstruct a Human 3-D Hypodermis: A Useful Tool for Pharmacological Functionality," Skin Pharmocol. Physiol., vol. 25, pp. 47-55, Oct. 2011.
Mardis, "New strategies and emerging technologies for massively parallel sequencing: applications in medical research," Genome Medicine, vol. 1, No. 4, p. 40, 2009.
Masukawa et al., "Comprehensive quantification of ceramide species in human stratum corneum," Journal of Lipid Research, vol. 50, No. 8, pp. 1708-1719, 2009.
Metzker, M. L., "Sequencing Technologies—The Next Generation," Nature Reviews Genetics, Jan. 2010, 11: 31-46.
Michel et al., "Characterization of a New Tissue-Engineered Human Skin Equivalent With Hair," In Vitro Cell Dev. Biol.-Animal, vol. 35, pp. 318-326, Jun. 1999.
Misery et al., "Definition of Sensitive Skin: An Expert Position Paper from the Special Interest Group on Sensitive Skin of the International Forum for the Study of Itch," Acta Derm Venereol, vol. 97, pp. 406, 2017.
Mosmann, "Rapid Colorimetric Assay for Cellular Growth and Survival: Application to Proliferation and Cytotoxicity Assays," Journal of Immunological Methods, vol. 65, pp. 55-63, 1983.
Nissan et al., "Functional melanocytes derived from human pluripotent stem cells engraft into pluristratified epidermis," PNAS, vol. 108, No. 36, pp. 14861-14866, Sep. 2011.
Nordback et al., "High Resolution Separation of Non-Polar Lipid Classes by HPLCELSD Using Alumina as Stationary Phase," J. High Resol. Chromatogr., vol. 22, No. 9, pp. 483-486, Sep. 1999.

(56) References Cited

OTHER PUBLICATIONS

Nordstrom et al., "Measurement of Sebum Output Using a Lipid Absorbent Tape," The Journal of Investigative Dermatology, vol. 87, No. 2, pp. 260-263, Aug. 1986.
O'Neill et al., "Analysis of Fatty Acid and Alcoholic Components of Sebaceous Lipid Types," Journal of Chromatographic Science, vol. 14, pp. 28-36, Jan. 1976.
Petritis et al., "Ion-pair reversed-phase liquid chromatography for determination of polar underivatized amino acids using perfluroinated carboxylic acids as ion pairing agent," Journal of Chromotography A, vol. 833, pp. 147-155, 1999.
Pihlak et al., "Rapid genome sequencing with short universal tiling probes," Nature Biotechnology, vol. 26, No. 6, pp. 676-684, Jun. 2008.
Piraud et al., "Ion-pairing reversed-phase liquid chromatography/ electrospray ionization mass spectrometric analysis of 76 underivatized amino acids of bilogical interest: a new tool for the diagnosis of inherited disorders of amino acid metabolism," Rapid Communications in Mass Spectrometry, vol. 19, pp. 1587-1602, 2005.
Ponec et al., "Lipid and ultrastructural characterization of reconstructed skin models," Int. J. Pharm., vol. 203, No. 1-2, pp. 211-225, Aug. 2000.
Ponec et al., "The Formation of Competent Barrier Lipids in Reconstructed Human Epidermis Requires the Presence of Vitamin C," The Journal of Investigative Dermatology, vol. 109, No. 3, p. 348-355, Sep. 1997.
Rainville et al., "Novel Application of Reversed-Phase UPLC-oaTOF-MS for Lipid Analysis in Complex Biological Mixtures: A New Tool for Lipidomics," Journal of Proteome, vol. 6, pp. 552-558, 2007.
Richters et al., "What Is Sensitive Skin? A Systematic Literature Review of Objective Measurements," Skin Pharmacology and Physiology, vol. 28, pp. 75-83, Oct. 2014.
Robosky et al., "Quantitative evaluation of sebum lipid components with nuclear magnetic resonance," Journal of Lipid Research, vol. 49, pp. 686-692, 2008.
Rosdy et al., "Retinoic Acid Inhibits Epidermal Differentiation When Applied Topically on the Stratum Corneum of Epidermis Formed in Vitro by Human Keratinocytes Grown on Defined Medium," in Vitro Toxicology, vol. 10, No. 1, pp. 39-47, Nov. 1997.
Schmalz et al., "Release of prostaglandin E2, IL-6 and IL-8 from human oral epithelial culture models after exposure to compounds of dental materials," Eur. J. Oral Sci., vol. 108, pp. 442-448, 2000.
Shendure, J., et al., "Next-generation DNA sequencing." Nature Biotechnology, Oct. 2008, 26(10): 1135-1145.
Shimizu, "Lipid Mediators in Health and Disease: Enzymes and Receptors as Therapeutic Targets for the Regulation of Immunity and Inflammation," Annu. Rev. Pharmacol. Toxicol., vol. 49, pp. 123-150, 2009.
Sullivan et al., "Complete Androgen Insensitivity Syndrome," Arch Opthalmol., vol. 120, pp. 1689-1699, Dec. 2002.

* cited by examiner

MODELS OF RECONSTRUCTED SENSITIVE SKIN

INTRODUCTION

The skin is a set of cells and macromolecules grouped together in the form of a resistant and flexible tissue, covering the entire body. It is formed of two joined layers, the epidermis and the dermis, with which subcutaneous tissues may be associated.

The epidermis, whose principal role is to protect the body, forms the uppermost layer of the skin and ensures the latter's impermeability and resistance. Four separate cellular layers can be identified in the skin: a basal layer (*Stratum basalis*), a spinous layer (*Stratum spinosum*), a granular layer (*Stratum granulosum*) and a corneal layer (*Stratum corneum*). While various cell types coexist in the epidermis, keratinocytes represent the large majority (90%). The characteristic activity of keratinocytes is synthesis of keratins, which are fibrous water-insoluble proteins making up 95% of all epidermal proteins.

The principal function of the skin is to establish a protective barrier against environmental attacks while allowing some exchanges between the internal environment and the external environment. The barrier function is provided first and foremost by the corneal layer (*Stratum corneum*), which makes the skin impermeable and hydrophobic, thus protecting the dermis from a massive influx of water. The corneal layer also resists chemical attacks. This layer is composed of cells, called corneocytes, which are dead and anucleate but filled with keratins and other products such as lipids, fatty acids and ceramides. Corneocytes are joined together by specific tight junctions, corneodesmosomes, forming a compact layer whose cohesion is further strengthened by a lipid cement. Under the granular layer, the tight junctions of the granular layer also participate in the skin barrier function (see, for example, Hogan et al., *J Allergy*, 2012: 901940, 2012).

Sensitive skin is a common syndrome in the population, but it lacks a clear definition. It is indeed a declarative syndrome, whose clinical manifestations are above all linked to feelings of discomfort (itching, tingling, burning, tightness . . . ). On the other hand, sensitive skin is usually not associated with objectively observable clinical symptoms, although it is often associated with red erythematous skin.

On a daily basis, the skin must face various attacks. It is exposed, for example, to chemical agents such as soap as well as physical stresses such as friction with clothing and exposure to the sun. Skin sensitivity seems to be triggered when the skin is subjected to different types of stress, such as exposure to the sun, certain chemicals, certain physical factors such as wool, cold, wind, etc. The clinical signs described above appear after exposure to these stress factors. Apart from these post-exposure manifestations, no studies have been able to demonstrate any difference, histological or physiological, between normal skin and sensitive skin in basal conditions.

Although the exact etiology of this syndrome is still poorly understood, it would appear that skin functions are abnormal or deficient in subjects with sensitive skin. According to the most commonly accepted hypotheses, sensitive skin is characterized by impaired barrier function, increased transcutaneous penetration, inflammatory and/or vascular hyperreactivity, and variations in nerve fiber density and response to stimuli (Richters et al., *Skin Pharmacol Physiol.* 2015, 28(2): 75-83). However, the factors mediating sensitive skin syndrome have not been identified today. In addition, the mechanisms leading to skin sensitivity are poorly understood. The most common hypothesis is that of greater permeability of the skin sensitive to the penetration of certain types of ingredients, leading to skin reactivity. The tolerance threshold for sensitive skin would be reduced, although this hypothesis has not been fully demonstrated.

In the absence of objective clinical signs, subjects with sensitive skin are generally identified by subjective self-assessment of a tingling sensation after application of lactic acid solution (Bererdesca et al., *Int J Cosmet Sci.* 2013, 35(1): 2-8). However, this type of test does not objectively define how the structure of sensitive skin differs from that of normal skin. Indeed, the different molecular and cellular mechanisms implemented in sensitive skin are still unknown. Diagnosis and treatment, therefore, are still as difficult.

There thus remains a need for a model that reproduces the clinical and structural features of sensitive skin.

DESCRIPTION

The present inventors have created a model of reconstructed skin that reproduces the features of sensitive skin as identified through an exhaustive clinical study.

Sensitive skin is a poorly known syndrome because it is largely based on subjective criteria. The inventors conducted a clinical study that allowed them to characterize the different cellular, molecular and physiological aspects of sensitive skin. In particular, they showed that sensitive skin in both children and adults is characterized by a strong induction of inflammation markers and an increase in transcutaneous water loss, indicating an alteration in barrier function.

Based on the results of this clinical study, the inventors developed a specialized in vitro skin model that can reproduce the biological features of sensitive skin and can be used to screen active ingredients or cosmetic or pharmacological formulations of interest.

The distinctive feature of the model of the invention is that it is similar to the real sensitive skin in that it includes a profile of inflammation markers very similar to that identified in subjects with sensitive skin. The same cytokines are induced in the model of the invention as in said subjects with sensitive skin.

The skin model of the invention is therefore particularly simple to implement. In addition, it does not require the use of a particular commercial cell line and is versatile and adaptable.

The particular features of the model of the invention allow the particularities of sensitive skin to be studied in vitro. In particular, the inventors observed that the application of exogenous stress to a reconstructed skin model induced physiological, cellular and molecular features similar to those observed in subjects with sensitive skin.

The term "subject" means any human person, whether an adult or a child. The term "child", according to the invention, means an individual 16 years of age or under. Thus, the category of children according to invention includes newborns aged 0 to 1 month, infants aged 1 month to 2 years, and children per se, aged at least 2 years. The term "newborn", as used herein, may equally well refer to a full-term or premature birth. To remove any ambiguity, the term "child" used in the present application without any further clarification should be understood in the most general meaning thereof, i.e., as referring to a person aged 16 or under. An "adult" according to the present invention is a person who is not a child, in order words a person over 16 years of age.

Preferably, the model according to the invention can be obtained with any type of sensitive skin, in particular without regard to the ethnic or geographic origin of the skin, or the phototype thereof. It may thus be of Caucasian, African, Asian, South American, Melanesian or other origin; it may further have the phototype I, II, III, IV, V or VI, without affecting the invention. Indeed, the invention aims at identifying biological markers characterizing any type of sensitive skin.

According to a first aspect, the invention therefore has as its object a model of reconstructed sensitive skin, said model being obtainable by a process comprising the steps of:
a) obtaining a reconstructed skin model from a skin sample from a subject; and
b) treating said reconstructed skin model from step a) with an exogenous stress.

"Exogenous stress" refers to any external factor affecting the integrity of the skin and which may lead, as the case may be, to a progressive decrease in the effectiveness of its functions. Exogenous stresses include, for example, pollutants, as well as ionizing and non-ionizing radiation. In particular, exogenous stress within the meaning of the present invention is a chemical substance whose topical application leads to an alteration in the structure and/or function of the skin. These agents are commonly used in clinical studies to characterize sensitive skin (Richters et al., Skin Pharmacol Pysiol, 2015, 28: 75-83). In particular, these agents can be used to define whether or not a person has sensitive skin. Such chemicals include agents such as lactic acid, sodium lauryl sulfate (SDS), capsaicin, menthol, benzoic acid, transcinnamic acid, octane, cumene, etc., methyl nicotinate and acetyl-b-methylcholine chloride (vasodilators), ethanol, allergens, skin occlusion factors, cocamidopropyl betaine, benzalkonium chloride (surfactants) and Peru balsam. Any of these agents can be used to generate the reconstructed sensitive skin model of the invention.

In particular, the inventors have shown that the application of lactic acid makes it possible to obtain a model of reconstructed skin that reproduces the features of sensitive skin. In particular, the application of lactic acid leads to a greater expression of inflammation markers without compromising the histological structure of the skin or affecting skin cell viability. The exogenous stress of the invention will therefore preferably be an application of lactic acid.

According to this preferred embodiment, the model of the invention is obtainable by a process comprising the steps of:
a) obtaining a reconstructed skin model from a skin sample from a subject; and
b) contacting said reconstructed skin model from step a) with lactic acid.

According to a preferred embodiment, the model of the invention is obtained by a process comprising the steps of:
a) obtaining a reconstructed skin model from a skin sample from a subject; and
b) contacting said reconstructed skin model from step a) with lactic acid.

Lactic acid can be used at any concentration to maintain the general structure of the skin while inducing the expression of inflammation markers. Preferably, the concentration of lactic acid used is between 0.05% and 5%, preferentially between 0.1% and 2.5%, more preferentially between 0.25% and 1.25%, notably between 0.4% and 0.8%. Lactic acid can be used in solution, at any concentration that maintains the general structure of the skin while inducing the expression of inflammation markers. Preferably, the concentration of lactic acid in the solution used should be between 0.05% and 5%, by weight of lactic acid/volume of solution. More preferably, lactic acid will be used at a concentration between 0.1% and 2.5%, even more preferably, at a concentration between 0.25% and 1.25%, even more preferably, at a concentration between 0.4% and 0.8%. According to the most preferred embodiment, lactic acid is used at a concentration of 0.6%, by weight of lactic acid/volume of solution.

According to an embodiment, said subject is an adult. In this case, the skin model of the invention is a model of adult skin. According to an embodiment, said subject is a child. In this case, the skin model of the invention is a model of child skin.

The model of reconstructed sensitive skin thus obtained is particularly advantageous because it faithfully reproduces the features of sensitive skin as they emerge from the clinical study conducted by the inventors.

"Sensitive skin" refers to a neurosensory skin condition that results in disparate clinical signs, including irritation, erythema or dry skin. More precisely, sensitive skin is a syndrome defined by the occurrence of unpleasant sensations, such as stings, burns, pain, pruritus or tingling, in response to stimuli that should not normally cause such sensations; in addition, sensitive skin is characterized by the absence of a link between these sensations and any skin pathology (Misery et al., Acta Derm Venereol 2017, 97: 4-6).

Sensitive skin is advantageously characterized by the expression of at least one biological marker.

In a preferred embodiment, the model of the invention expresses at least one biological marker.

According to another preferred embodiment, the model of the invention is obtainable by a process comprising the steps of:
a) obtaining a reconstructed skin model from a skin sample of a subject;
b) contacting said reconstructed skin model from step a) with lactic acid; and
c) measuring the expression level of at least one biological marker.

Advantageously, said model of reconstructed sensitive skin of the invention is obtained by the process for preparing a model according to the present invention described below.

In the sense of the invention, "biological marker" refers to a feature that is objectively measured and evaluated as an indicator of normal biological processes, pathogenic processes, or pharmacological responses to a therapeutic intervention. A biological marker therefore refers to a range of different substances and parameters. For example, a biological marker may be a substance whose detection indicates a particular disease state (for example the presence of reactive C protein as a marker of infection), or on the contrary a substance whose detection indicates a specific physiological state. The biological marker according to the invention is preferably a gene, the products of a gene such as its transcripts and peptides from its transcripts, a lipid, a sugar or a metabolite.

The skilled person seeking to determine the class to which a biological marker belongs will be able to easily consult the relevant scientific literature or refer to public databases such as, for example, those grouped on the website of the National Center for Biotechnology Information (http://www.ncbi.nlm.nih.gov/guide/).

The inventors have particularly selected markers whose level of expression shows a marked variation between sensitive and normal skin. The selected markers are therefore of particular interest in the method of the invention, their expression being measured in a skin model that faithfully reproduces the features of sensitive skin.

In particular, the inventors have shown that markers of inflammation are particularly expressed in sensitive skin. Inflammation is a normal defense reaction of the body, but it can contribute to the reduction of skin integrity. In addition, the inventors have shown that the expression of the barrier markers is decreased compared to normal skin. Finally, the markers of immunity, including those of innate immunity and defense, are also affected and with them the skin's ability to react to external insult.

The biological marker of the invention is therefore advantageously a marker selected from the group of inflammation markers, barrier function markers, and innate immunity and defense markers.

More specifically, the model of reconstructed sensitive skin of the invention is characterized in that, in said model:
a) the expression of the biological marker selected from the group of inflammation markers is higher than in normal skin, and/or
b) the expression of the biological marker selected from the group of barrier markers is lower than in normal skin; and/or
c) the expression of the biological marker selected from the group of innate immunity and defense markers is lower than in normal skin.

According to another specific embodiment, the model is obtained by a process in which the expression of at least one biological marker selected from the group of inflammation markers, barrier function markers and innate immunity and defense markers is measured.

In addition, the inventors have shown that markers of inflammation are particularly expressed in sensitive skin. Inflammation is a normal defense reaction of the body, but it can contribute to the reduction of skin integrity. In addition, the inventors have shown that at the same time, the expression of the barrier markers is decreased compared to normal skin. Finally, the markers of defense and innate immunity are also affected and with them the skin's ability to react to external insult.

In the sense of the invention, "markers of skin inflammation" means markers whose variation in expression correlates with skin inflammation. "Inflammation", according to the invention, refers to all the reactive defense mechanisms by which the body recognizes, destroys and eliminates all substances that are foreign to it. "Skin inflammation" refers more specifically to a reaction of the immune system in response to an attack on the skin, such as an environmental attack, which may or may not cause a wound, or even vascular damage if it occurs. Skin inflammation can manifest itself as erythema, characterized by redness associated with local vasodilation, edema, characterized by swelling, and a feeling of heat. In addition, skin inflammation is accompanied by a variation in the level of expression or concentration of gene, protein or lipid markers well known to the skilled person, which may refer, for example, to Vahlquist (*Acta Derm Venereol;* 80: 161; 2000).

The initiation and continuation of inflammation, its spread from the initial site, requires inflammatory markers that are locally synthesized or that are inactive precursors in the circulation. "Inflammatory marker" means here a substance synthesized and released by a cell of the organism acting on a cell of the same organism that has a specific receptor for this substance and involved in the processes of inflammation of said organism. Several stages in the inflammatory response can be distinguished. Thus, skin inflammation according to the invention involves at least two distinct components, the tissue component and the vascular component.

"Tissue component" of skin inflammation means here the local skin process of defense against insult. The tissue component of inflammation involves both protein and lipid inflammatory markers. "Protein markers", or "inflammatory protein markers", or "protein markers of the tissue component of inflammation", are defined here as inflammatory markers of a peptide or protein nature, such as cytokines IL-1, IL-2, IL-6, IL8 and TNFα, the complement system, or proteins involved in coagulation, if applicable. "Lipid markers", or "inflammatory lipid markers", or "lipid markers of the tissue component of inflammation", are defined here as inflammatory markers of a lipidic nature, including prostaglandins and leukotrienes, both of which are synthesized from arachidonic acid, as well as the activation of the enzymes responsible for this production (Shimizu, *Annu Rev Pharmacol Toxicol.*, 49: 123-150, 2009). The inflammatory protein and lipid markers thus produced will induce a cascade of reactions within the skin involving other inflammation cells, in particular immune and vascular cells. The clinical result includes redness and even edema.

During the inflammatory reaction, the blood and lymph vessels in the skin first dilate. This phase is followed by an increase in permeability, causing water and salts from the blood or lymphatic vessel to move towards the tissue and resulting in the formation of edema. "Vascular component" means here this process of vasodilation followed by an increase in vascular permeability. The vascular component of inflammation includes in particular the different steps leading to extravascular migration of different types of leukocytes such as $CD4^+$, $CD8^+$, $CD4CD8^-$, NK and B-lymphocytes, monocytes, neutrophils, eosinophils or basophils.

The marker for skin inflammation according to the invention is preferably selected from the protein markers of the tissue component of inflammation, the lipid markers of the tissue component of inflammation and the markers of the vascular component of inflammation.

The protein markers of the tissue component of inflammation are well known to the skilled person. They include cytokines such as TNFα or interleukins, including IL-1, L-1RA, IL-2, IL-6, IL-8, and matrix metalloproteases such as MMP1a and MMP3. Preferably, the protein marker of the tissue component of inflammation is selected from the group consisting of interleukins, preferably IL1α, IL1RA and IL8.

Human interleukin IL1α has a protein sequence represented by the reference sequence NCBI: NP_000566. This protein is encoded by the human ILL& gene (NCBI reference: Gene ID: 3552), whose sequence corresponds to the NCBI reference: NM_000575. Interleukin IL1α is the primary inflammatory marker of the inflammatory cascade. This cytokine secreted by many cells in response to inflammatory stress. It is expressed constitutively by keratinocytes, where it is stored in the cytoplasm. It can be passively released in response to acute stress, such as membrane disruption. However, more moderate stress can also cause an increase in the synthesis of this cytokine.

The IL1A (IL1 receptor antagonist) protein is a protein belonging to the same family as IL1α. Its protein sequence is represented by the reference sequence NCBI: NP_000568. This protein is encoded by the human IL1RN gene (NCBI reference: Gene ID: 3557), whose sequence corresponds to the NCBI reference: NM_000568. The IL1RA protein is expressed by epithelial cells. It is induced in particular in response to irritation, secondary to IL1α. The balance of the IL1RA/IL1α ratio is particularly important for maintaining skin homeostasis. Indeed, IL1RA binds to the IL1α receptor without activating it, thus attenuating the response induced by IL1α.

IL8 protein is a cytokine that is absent from healthy skin but is induced early in skin inflammation. It is produced by de novo synthesis in keratinocytes stimulated by IL1α or TNF. As a result, it is a predictive marker of a biological response, even in the absence of visible signs of skin irritation. The protein sequence of human IL-8 interleukin corresponds to the reference sequence NCBI: NP_000575. This protein is encoded by the human IL8 gene (NCBI reference: Gene ID: 3576). Its sequence is accessible under the reference NCBI: NM_000584.

As explained above, the cutaneous immune system is regulated by inflammatory markers such as bioactive lipids that can trigger a rapid immune response with controlled inflammation, followed by effective resolution. Lipid markers represent all of these inflammatory lipid markers, as well as the enzymes affecting their metabolism. They include fatty acids, including polyunsaturated fatty acids, including ω-6 and ω-9, leukotrienes, prostaglandins, as well as proteins involved in the metabolism of these lipids, such as phospholipase PLA2G2F, synthase PTGS2 or glutathione S-transferase MGST1.

The inflammatory lipid marker is advantageously selected from polyunsaturated fatty acids, in particular ω-6 and ω-9, prostaglandins, including in particular prostaglandin E2, PLA2G2F, and MGST1.

Polyunsaturated fatty acids contribute to the transmission of the inflammatory signal. Polyunsaturated fatty acids ω-6, and incidentally ω-9, thus have a proinflammatory role. Arachidonic acid is therefore at the heart of the lipid inflammation cascade. This 20:4 (ω-6) fatty acid is released from the membrane phospholipids of inflammatory cells under the action of phospholipases A2. Its metabolism, particularly through the formation of several of its oxygenated derivatives, is associated with proinflammatory conditions. Other polyunsaturated fatty acids that can be used as markers of lipid inflammation include linoleic acid (18:2, ω-6) and oleic acid (18:1, ω-9).

Prostaglandin E2 (PGE2), is a well-known derivative of arachidonic acid obtained by the action of cyclooxygenase. There are two cyclooxygenase (COX) isoforms: cyclooxygenase 1 which is constitutive in tissues and cyclooxygenase 2 which is induced by inflammatory phenomena. Proinflammatory stimulation (trauma, cytokines . . . ) thus leads to the synthesis of PGE2 which is responsible for vasodilation (generating redness and edema), sensitization of nociceptors to bradykinin and histamine (responsible for pain) and fever (with cytokines IL1 and IL6).

The markers of the vascular component of inflammation correspond to molecules that are involved in the vasodilation and vascular permeability enhancement processes characteristic of vascular inflammation. They include proteins such as VEGF-A, FGF2, THBS1, VIPR1, ADCYAP1. The marker for vascular inflammation is vascular endothelial growth factor A (VEGF-A). This protein is produced by the keratinocyte in response to an attack. It stimulates the proliferation of endothelial cells through its angiogenic activity, as well as vascular permeability. In fact, the overexpression of VEGF-A leads to the extrusion of blood.

The present inventors have also shown that the expression of barrier function markers is reduced in sensitive skin.

"Barrier markers" according to the invention include markers that are specifically expressed in the outermost layers of the epidermis and that participate in the barrier function.

As is well known to the skilled person, the main function of the skin is to establish a protective barrier against environmental damage while allowing certain exchanges between the internal and external environment. This barrier function is mainly carried by the *Stratum corneum* of the epidermis.

The *Stratum corneum* is the final product of epidermal differentiation, where keratinocytes are transformed into corneocytes; these corneocytes are coated with an intercellular lipid matrix composed of ceramides, cholesterol and essential fatty acids. After extrusion of the lamellar bodies, the lipid precursors are metabolized to mature lipids. In the case of ceramide precursors, it is the acid sphingomyelinase and beta glucocerebrosidase enzymes that transform them into ceramides 2 and 5 (for sphingomyelinase) and ceramides 1, 3, 4, 6, 7, 8 and 9 (for glucocerebrosidase). Corneocytes are surrounded by a corneal protein envelope composed of many proteins such as involucrin, loricrin, small proline-rich proteins and sciellin in particular, firmly bound under the action of transglutaminases. However, under the *Stratum corneum*, the tight junctions constitute a second line of barrier function. These junctions constitute a selective paracellular diffusion barrier at the *Stratum granulosum*, preventing the penetration of harmful molecules. The tight junctions are composed of different transmembrane proteins such as claudins, occludin and ZO1.

The barrier functions carried by the *Stratum corneum* and the tight junctions are closely related. Indeed, the alteration of one or the other can influence the formation of the other. Preferably, the markers of the barrier function according to the invention are markers expressed in the *Stratum corneum* or markers expressed in the tight junctions of the *Stratum granulosum*. These markers include claudins, including claudin-1 (CLDN1), transglutaminases, such as transglutaminase 1 (TGM1), keratins, including keratin 1 (KRT1) and keratin 10 (KRT10), peptidyl arginine deiminase type 1 human (PAD1), caspase 14 (CASP14), aquaporin 3 (AQP3), loricrin (LOR), sciellin (SCEL), BARX Homeobox 2 (BARX2), desmoglein-1 (DSG1), filaggrin (FLG), involucrin (IVL), sphingomyelinase or sphingomyelin diesterase (SMPD), corneodesmosin (CSDN), etc.

In a more preferential embodiment, said marker of the epidermal barrier is involucrin (IVL). Involucrin, whose peptide sequence is the reference sequence NCBI: NP_005538.2, is expressed in horny-granular layers. It is the first precursor of the corneal envelope which represents 5 to 15% of the corneal envelope, and also serves as a link with the lipidic corneal envelope. It is encoded by the IVL gene (Gene ID: 3713), whose sequence has the reference NCBI: NM_005547.2.

The inventors also showed that the amount of skin lipids was decreased in a sensitive skin model. In the *Stratum corneum*, lipids are arranged in a lamellar plane in the spaces between the corneocytes, thus forming a cement that helps protect the skin against external insult and maintain a good level of intra-epidermal water. These lipids are phospholipids, cholesterol and glucosylceramides, which are modified in the inter-corneocyte spaces by specialized enzymes, ceramides, cholesterol, cholesterol sulfate and free fatty acids (Jungerstend et al., *Contact Dermitis*, 58(5): 255-262, 2008). Ceramides, sterols and free fatty acids are also found in sebum, among other components. Finally, the skin's surface is covered with a protective film that allows the skin to maintain its moisture and protect itself against external insult. This surface skin film includes, among other things, a hydrolipidic film, which consists essentially of sweat, water, sebum and other lipids. These include ceramides, triglycerides and fatty acids in approximately equal proportions.

According to a particular embodiment, the barrier marker according to the invention is therefore a lipid marker. "Lipids" refers here to any natural fat-soluble (i.e. lipophilic) molecule. Lipids are a heterogeneous group of compounds with many essential biological functions. Lipids can be defined more specifically as small hydrophobic or amphiphilic molecules, which come entirely or partially from ketoacyl or isoprene groups. For an overview of all lipid classes, refer to the "Lipid Metabolites and Pathways Strategy (LIPID MAPS) classification system" (National Institute of General Medical Sciences, Bethesda, MD). In particular, the lipid marker according to the invention is selected from ceramides, phospholipids, glucosylceramides, sterols, triglycerides and free fatty acids. Even more preferably, the lipid marker according to the invention is selected from ceramides.

A "ceramide" according to the invention is a lipid resulting from the amidification reaction of sphingosine and a fatty acid. A ceramide therefore consists of a sphingosine or phytosphingosine base linked by an amide bond to α-hydroxy, ω-hydroxy or non-hydroxy acids having variable hydrophobic chain lengths. In human Stratum corneum, 9 classes of ceramides, referred to as CER 1 to 9, have been identified (see for example Dayan, Cosm & Toil, 121(1): 37-44, 2006; Jungerstend et al., Contact Dermitis, 58(5): 255-262, 2008; Farwick et al., Cosm & Toil, 124(2): 63-72; Masukawa et al., J Lipid Res., 50(8): 1708-1719, 2009). The ceramide according to the invention is more preferentially selected from the group consisting of said ceramides CER1 to 9.

On the other hand, the present inventors have shown that NMFs are affected in sensitive skin. The natural moisturizing factor, or NMF, is derived from the proteolysis of filaggrin according to a cascade of reactions involving enzymes including caspase 14 and peptidylarginine deiminase (PAD1). NMF is a mixture of hygroscopic substances with water-retaining properties (Fluhr et al., Exp Dermatol., 19(6): 483-492, 2010). Among these, the sodium salt of pyrrolidone carboxylic acid or PCA Na (from the cyclisation of glutamic acid released by the decomposition of profilaggrin) and lactates are the most hygroscopic substances. NMF also includes free amino acids (serine, citrulline . . . ), citrates and formates, urea, ions, nitrogen, uric acid, glycosamine, creatinine, phosphates, as well as compounds yet unidentified. The amount of NMF can be measured by all methods known to the skilled person, particularly by Raman microspectroscopy. According to another preferred embodiment, the marker of the barrier according to the invention is therefore NMF.

The barrier marker according to the invention is therefore preferably involucrin, a ceramide selected from the group of ceramides CER 1 to 9 or NMF.

The present inventors have also shown that the expression of immune markers is reduced in sensitive skin.

"Immune marker" refers here to all markers used to determine the identity of the organism and to defend it from the outside. These markers serve as the first line of defense against bacterial infections. They include proteins such as defensins, beta defensins, including beta defensins 1 and 2 (BD-1 and BD-2), Toll receptors, such as Toll-like receptor 2 and S100A7 protein. An immune marker according to the invention is preferably beta-defensin 2, protein S100A7 or Toll-like receptor 2.

Beta-defensin 2 (BD-2), which is also called skin-antimicrobial peptide 1 (SAP1), is a peptide encoded by the DEFB4 gene (NCBI reference: Gene ID: 1673). The sequence of human beta-defensin 2 is available under accession number NP_004933, while the sequence of the DEFB4 gene is available under accession number NM_004942.

S100A7 protein, for S100 calcium binding protein A7 (sequence NP_002954), is a protein of the S100 family of proteins, which are proteins that bind calcium through their EF hands units. It is encoded by the S100A7 gene (NCBI reference: Gene ID: 1673) of sequence NM_002963.

The Toll-like receptor 2 or TLR2 protein (sequence NP_003255.2) is a membrane receptor, which is expressed on the surface of certain cells. It recognizes foreign substances, including bacterial lipoproteins. The activation of TLR2 leads to the synthesis of cytokines, in particular interleukin 6. TLR2 is encoded by the TLR2 gene (NCBI reference: Gene ID: 6278) of sequence: NM_003264).

It will also be obvious to the skilled person that the sensitive skin model will all the more accurately reproduce the existing situation in vivo if it expresses a large number of markers of different types among the above markers.

According to a preferred embodiment, the skin model of the invention is obtained by a process comprising a step c) of measuring the expression level of a combination of biological markers. Said combination according to the invention comprises or consists of:

at least one skin inflammation marker and at least one barrier marker as defined above; or at least one skin inflammation marker and at least one immune marker, as defined above; or at least one barrier marker and at least one immune marker, as defined above.

In a more preferential embodiment, said combination includes at least one skin inflammation marker and at least one barrier marker and at least one immune marker, as defined above.

The use of marker combinations comprising at least one marker of each of the different types indicated above is particularly advantageous.

For each of these markers, the term "level of expression" refers to the cellular concentration of said marker. Thus, the expression level of prostaglandin E2, a ceramide or a polyunsaturated ω-6 or ω-9 fatty acid corresponds to the concentration of said lipid in the cell. If the marker is a gene, the "level of expression" in the sense of the invention corresponds to the cellular concentration of at least one of the products of the gene of the marker. More precisely, the expression level of said biological marker corresponds to the amount or cellular concentration of the transcript of said gene or protein from said transcript. According to a preferred embodiment, the expression level of said biological marker corresponds to the amount or cellular concentration of the transcript of said gene. According to another embodiment, the expression level of said biological marker corresponds to the amount or cellular concentration of the protein derived from said transcript.

In the sense of the present application, "measuring the expression level of a combination of biological markers" means measuring the expression level of each of the markers of the combination. The expression of a gene can be measured, for example, at the nucleotide level, by measuring the amount of transcripts of said gene, and can also be measured, for example, at the peptide level, by measuring the amount of proteins derived from said transcripts. Therefore, in the sense of the invention, "measuring the expression level of said gene" means measuring the amount or cellular concentration of the product of the gene in its peptide form or in its nucleotide form.

In general, the expression of the biological marker according to the invention will be detected in vitro from the reconstructed skin model.

In a particular embodiment, the process of the invention may comprise one or more intermediate steps between obtaining the reconstructed skin model and measuring the expression of the biological marker, said steps corresponding to the extraction from said reconstructed skin model of a lipid sample, an NMF sample, an mRNA (or corresponding cDNA) sample or a protein sample. This can then be used directly to measure the expression of the marker. The preparation or extraction of mRNA (as well as its reverse-transcription into cDNA), proteins, lipids or NMFs from a sample of skin cells are routine procedures well known to the skilled person.

For some lipid markers such as prostaglandin E, it may not even be necessary to prepare a lipid sample. Indeed, this marker is secreted in the culture medium. It is then easy for the skilled person to determine the prostaglandin E2 from said culture medium. Several methods for the determination and quantification of prostaglandin E2 have thus been described in the art, including in particular ELISA methods. Such a method, to which the skilled person may refer, is therefore detailed in the experimental part of the present application. It should also be noted that kits are commercially available for the determination of prostaglandin E2 (for example, at Cisbio Assays or Pierce).

Once a sample of mRNA (or corresponding cDNA) or protein is obtained, marker expression at the level of either mRNA (i.e. all mRNAs or cDNAs present in the sample) or proteins (i.e. all proteins present in the sample) can be measured. The method used to this end then depends on the type of transformation (mRNA, cDNA or protein) and the type of sample available.

When marker expression is measured at the mRNA (or corresponding cDNA) level, any technology usually used by the skilled person can be implemented. These technologies for analyzing the level of gene expression, such as transcriptome analysis, include well-known methods such as PCR (Polymerase Chain Reaction, if starting from DNA), RT-PCR (Reverse Transcription-PCR, if starting from RNA) or quantitative RT-PCR or nucleic acid chips (including DNA chips and oligonucleotide chips) for a higher throughput.

"Nucleic acid chips" refers here to several different nucleic acid probes that are attached to a substrate, which may be a microchip, a glass slide, or a bead the size of a microsphere. The microchip can be made of polymers, plastics, resins, polysaccharides, silica or a material based on silica, carbon, metals, inorganic glass, or nitrocellulose.

Probes can be nucleic acids such as cDNA ("cDNA chip"), mRNA ("mRNA chip") or oligonucleotides ("oligonucleotide chip"), which oligonucleotides can typically have a length between about 25 and 60 nucleotides.

To determine the expression profile of a particular gene, a nucleic acid corresponding to all or part of said gene is labeled and then contacted with the chip under hybridization conditions, leading to the formation of complexes between said labeled target nucleic acid and probes attached to the surface of the chip that are complementary to that nucleic acid. The presence of marked hybrid complexes is then detected.

These technologies make it possible to monitor the expression level of a particular gene or several genes or even all genes in the genome (full genome or full transcriptome) in a biological sample (cells, tissues . . . ). These technologies are routinely used by the skilled person and therefore there is no need to detail them here. Exemplary embodiments of the invention based on gene expression analysis (cDNA chips) and quantitative PCR are described in the experimental section.

Alternatively, it is possible to use any current or future technology to determine gene expression based on the amount of mRNA in the sample. For example, the skilled person can measure the expression of a gene by hybridization with a labeled nucleic acid probe, such as northern blot (for mRNA) or Southern blot (for cDNA), but also by techniques such as the serial gene expression analysis method (SAGE) and its derivatives, such as LongSAGE, SuperSAGE, DeepSAGE, etc. It is also possible to use tissue chips (also known as TMAs: "tissue microarrays"). The tests usually used with tissue chips include immunohistochemistry and in situ fluorescent hybridization. For mRNA analysis, tissue chips can be coupled with in situ fluorescent hybridization. Finally, it is possible to use massive sequencing in parallel to determine the amount of mRNA in the sample (RNA-Seq or "Whole Transcriptome Shotgun Sequencing"). To this end, several massive parallel sequencing methods are available. Such methods are described in, for example, U.S. Pat. Nos. 4,882,127; 4,849,077; 7,556,922; 6,723,513; WO 03/066896; WO 2007/111924; US 2008/0020392; WO 2006/084132; US 2009/0186349; US 2009/0181860; US 2009/0181385; US 2006/0275782; EP-B1-1141399; Shendure & Ji, *Nat Biotechnol.*, 26(10): 1135-45, 2008; Pihlak et al., *Nat Biotechnol.*, 26(6): 676-684, 2008; Fuller et al., *Nature Biotechnol.*, 27(11): 1013-1023, 2009; Mardis, *Genome Med.*, 1(4): 40, 2009; Metzker, *Nature Rev. Genet.*, 11(1): 31-46, 2010.

When marker expression is measured at the protein level, specific antibodies can be used, particularly in well-known technologies such as immunoprecipitation, immunohistology, western blot, dot blot, ELISA or ELISPOT, protein chips, antibody chips, or tissue chips coupled to immunohistochemistry. Other techniques that may be used include FRET or BRET techniques, flow cytometry, microscopy or histochemistry methods, including confocal microscopy, fluorescence microscopy, electron microscopy, atomic force microscopy, methods based on the use of one or more excitation wavelengths and an appropriate optical method, as an electrochemical method (voltammetry and amperometry techniques), and radiofrequency methods, such as multipolar, confocal and non-confocal resonance spectroscopy, such as fluorescence, luminescence, chemiluminescence, absorbance, reflectance, transmittance, birefringence or refractive index (for example, by surface plasmon resonance, by ellipsometry, by resonant mirror method, etc.), radioisotopic or magnetic resonance imaging, analysis by polyacrylamide gel electrophoresis (SDS-PAGE); two-dimensional electrophoresis, spectrophotometry, mass spectrometry and tandem mass spectrometry, liquid or gas chromatography coupled with mass spectrometry or tandem mass spectrometry. All these techniques are well known to the skilled person and it is not necessary to detail them here.

If the biological marker is a lipid, such as a ceramide or fatty acid, the skilled person may use all available methods to measure the lipid content in a sample of skin cells. These methods include, among others, liquid chromatography (HPLC, see for example Sullivan et al., *Arch Ophthalmol.* 120(12): 1689-99, 2002), liquid chromatography coupled with an evaporative light scattering detector (HPLC-ESD, see Nordbäck et al., *J. High Resolut. Chromatogr.* 22: 483-486, 1999; Torres et al. *J. Chromatogr. A.* 1078: 28-34, 2005); thin-layer chromatography (TLC, for example Downing et al., *J Invest Dermatol,* 77(4): 358-360, 1981; Nordstrom et al., *J Invest Dermatol.* 87(2): 260-263, 1986);

nuclear magnetic resonance (NMR, see for example Robosky et al., *J Lipid Res.*, 49(3): 686-692, 2008); confocal Raman microspectroscopy in vivo; mass spectrometry, gas chromatography coupled to mass spectrometry (GC-MS, see O'Neill et al., *J Chromatogr Sci*, 14(1): 28-36, 1976); gas chromatography coupled with a flame ionization detector; liquid chromatography coupled with mass spectrometry (see for example van Smeden et al., *J Lipid Res*, 52(6):1211-1221, 2011); ultra-performance liquid chromatography (UPLC, see Rainville et al., *J Proteome Res*, 6(2):552-558, 2007; Castro-Perez et al., *J Proteome Res.*, 10(9): 4281-4290, 2011). The organization of these lipids in the skin and more particularly in the *Stratum corneum* (or corneal layer), a lamellar or lateral organization, can also be analyzed by techniques such as X-ray diffraction (Bouwstra et al., *J Invest Dermatol.* 97(6): 1005-1012, 1991; van Smeden et al., *J Lipid Res.*, 52(6):1211-1221, 1991) or by Fourier transform infrared spectroscopy (Gorcea et al., *Int J Pharm*. Nov. 10, 2011) or by morphometric analysis in electron microscopy (Daehnhardt-Pfeiffer et al., *Skin Pharmacol Physiol.*, 25(3): 155-161, 2012) or by electron microscopy analysis of the vitreous section of skin combined with molecular analysis (Iwai et al., *J Invest Dermatol.*, Apr. 26, 2012).

The determination of NMF is a procedure well known to the skilled person. In particular, it is possible to determine NMF by using confocal Raman microspectroscopy in vivo. It is a procedure commonly used in the field for at least 15 years. Examples include publications by Caspers et al. (*J Invest Dermatol.*, 116(3): 434-442, 2001), Vyumvuhore et al. (*J Biomed Opt.*, 19(11): 111603, 2014), and Falcone et al. (*Skin Pharmacol Physiol*, 28: 307-317, 2015). It is also possible to determine NMFs by liquid chromatography coupled with mass spectrometry. Examples include Piraud et al. (*Rapid Commun Mass Spectrom*, 19(12):1587-602, 2005), Petritis et al. (*Journal of Chromatography A*, 833(2): 147-155, 1999), Henriksen et al. (*J Am Soc Mass Spectrom*, 16(4): 446-455, 2005) and Yang (Application of biophysics and bioengineering to the assessment of skin barrier function. Thesis (Doctor of Philosophy (PhD)). University of Bath, UK, 2011).

The sensitive skin model according to the invention is a reconstructed skin model in which the expression of the above markers is increased or decreased, depending on the marker, compared to normal skin.

"Normal skin" means skin from a healthy subject. In order to avoid any ambiguity, it should be specified that sensitive skin is not normal skin within the meaning of the present invention.

The term "increased", as used here in some embodiments, means a larger amount, for example, a amount slightly greater than the original amount, or for example a amount in great excess of the original amount, and in particular all amounts in the interval. Alternatively, "increase" may refer to a amount or activity that is at least 1%, 2%, 3%, 4%, 5%, 6%, 7%, 8%, 9%, 10%, 11%, 12%, 13%, 14%, 15%, 16%, 17%, 18%, 19% or 20% greater than the amount or activity for which the amount or increased activity is compared, or at least 30%, 40%, 50%, 60%, 70%, 80%, 90%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 900%, 950%, 1,000%, 1,100%, 1,200%, 1,300%, 1,400%, 1,500%, 1,600%, 1,700%, 1,800%, 1,900% or 2,000% more than the amount or activity for which the increased amount or activity is compared. The terms "increased", "greater than", and "increased" are used interchangeably here.

The term "decreased", as used here in some embodiments, means a smaller amount, for example, a amount slightly less than the original amount, or for example a much smaller amount than the original amount, including all amounts in the interval. Alternatively, "decrease" may refer to a amount or activity that is at least 1%, 2%, 3%, 4%, 5%, 6%, 7%, 8%, 9%, 10%, 11%, 12%, 13%, 14%, 15%, 16%, 17%, 18%, 19% or 20% less than the amount or activity for which the decreased amount or activity is compared, or at least 30%, 40%, 50%, 60%, 70%, 80%, 90%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 900%, 950%, 1,000%, 1,100%, 1,200%, 1,300%, 1,400%, 1,500%, 1,600%, 1,700%, 1,800%, 1,900% or 2,000% less than the amount or activity for which the decreased amount or activity is compared. The terms "decreased", "smaller than", and "reduced" are used interchangeably here.

In order to determine whether the expression of a marker is increased or decreased in the sensitive skin model of the invention, the expression level of said marker may be compared with a reference expression level.

According to this preferred embodiment, the sensitive skin model of the invention is obtained by a process further comprising a step d) of comparing the expression level of the biological marker in step c) with a reference expression level.

A "reference expression level of a biological marker" means, in the sense of the present application, any level of expression of that marker used as a reference. For example, a reference expression level can be obtained by measuring the expression level of the marker of interest in a normal skin model. Such a normal skin model may, for example, correspond to a reconstructed skin model obtained from a skin sample from a healthy subject. The reconstructed skin model from step a) before contact with lactic acid can also be used as a normal skin model. In this case, the expression of the biological marker is measured before step b); the level thus determined is then the reference expression level of said biological marker.

In other embodiments, the reference expression level of a biological marker corresponds to the expression level of said marker in the sensitive skin model in the absence or presence of a particular treatment. For example, in a particular embodiment, the reference expression level of a biological marker is obtained by measuring the expression of said marker in the sensitive skin model that has not been contacted with an active ingredient or formulation. In another particular embodiment, the expression of said marker is measured in the sensitive skin model treated with an active ingredient or formulation known to be effective against sensitive skin.

The skilled person will also easily understand that the comparison in step d) is preferably made between measurements of levels of expression obtained for skin models obtained from skin samples of similar or even identical histological structures. In the sense of the present application, "similar histological structures" means that the relative proportions of the cell types included in the compared skin models are similar. Thus, it is preferable that the relative proportions of the cell types included in the skin model of step a) do not differ by more than 5% from the relative proportions of the cell types included in the skin model used to obtain the reference expression level of step d). In the sense of the present application, "relative proportion of a cell type" means the ratio of the number of cells corresponding to that cell type to the total number of cells included in the skin model. Thus, for example, it is preferable that the proportion of keratinocytes on the total cell count in the skin model of step a) does not differ by more than 5% from the proportion of keratinocytes on the total cell count in the skin model used to obtain the reference expression level in step d). In the sense of the present application, "identical histological structures" means that the relative proportions of the cell types included in the compared skin models are identical. In the sense of the present invention, the relative proportions of the cell types included in the nipple skin model of step a) are identical to the relative proportions of the cell types included in the skin model used to obtain the reference expression level of step d) when they differ by no more than 0.1%. Advantageously, the proportion of keratinocytes on the total cell count in the skin model of step a) does not differ by more than 0.1% from the proportion of keratinocytes on the total cell count in the skin model used to obtain the reference expression level in step d).

The skilled person will understand just as easily that the comparison in step d) is preferably made between measurements of levels of expression obtained for skin models that are of similar or even identical height, volume or weight. Thus, it is preferable that the size, volume, or weight of the skin model of step a) does not differ by more than 5% from the size, volume, or weight of the skin model used to obtain the reference expression level of step d). More preferably, the size, volume and weight of the skin model of step a) will not differ by more than 5% from the size, volume and weight of the skin model used to obtain the reference expression level in step d). More preferably, the size, volume and weight of the skin model of step a) will not differ by more than 0.1% from the size, volume and weight of the skin model used to obtain the reference expression level in step d).

Alternatively, if the skin models differ by more than 5% in height, volume and weight, the skilled person can normalize the level obtained in step c) and the reference level of step d) using a normalization factor.

This normalization factor could, for example, be a directly accessible physical marker such as the mass of cells in the sample, or the mass of a cellular component such as the mass of cellular DNA or the mass of cellular proteins.

It may also be advantageous to use as a normalization factor the expression level of a gene that is expressed at the same level in almost all cells of the body. In other words, according to a particular embodiment of the present invention, the expression level of a housekeeping gene is used as a normalization factor. According to another embodiment, the level obtained in step c) and the reference level of step d) are normalized using the level of expression, not of housekeeping genes, but of the proteins encoded by them. A housekeeping gene is a gene expressed in all cell types, which encodes a protein with a basic function necessary for the survival of all cell types. A list of human housekeeping genes can be found in Eisenberg et al. (*Trends in Genet*, 19: 362-365, 2003). Housekeeping genes according to the invention include, for example, RPS28, GAPDH, B2M, TFRC, YWHAZ, RPLO, 18S, GUSB, UBC, TBP, GAPDH, PPIA, POLR2A, ACTB, PGK1, HPRT1, IPO8 and HMBS.

In the sense of the invention, the reconstructed skin model obtained from a skin sample may be any tissue model comprising skin cells, in particular keratinocytes, and in which said skin cells have been obtained from a skin sample.

In the sense of the invention, "skin sample" means any sample containing skin cells. The skin samples according to the invention therefore include both fresh skin explants obtained directly from the patient, as well as suspended skin cell cultures, monolayer skin cell cultures, bilayer skin cell cultures and tissue models, including reconstructed skin cultures and reconstructed mucosal cultures. As it is often difficult to work on fresh explants, it is particularly advantageous, in the context of the present invention, to use skin cell cultures. Advantageously, skin cells according to the invention include normal, healthy or pathological cells, or cells from lineages. For example, cultured skin cells may be cells obtained from skin tissue explant. "Explant" or "skin explant" means a sample of skin cells or tissue, which can be taken for surgical purposes or for analysis.

In particular, an explant can be obtained during surgical excision. "Excision" means a surgical procedure consisting in cutting (excising) a more or less wide or deep part of the skin to treat an abnormality or growth. An excision is performed either to remove a cancerous or suspicious tumor or to treat a benign skin abnormality that is embarrassing, whether for functional or aesthetic reasons. An excision in the sense of the invention includes, for example, skin samples obtained after plastic surgery (mammoplasty, abdominoplasty, facelift, circumcision, otoplasty, i.e. ear pinning, syndactyly or supernumerary finger, etc.).

An explant can also be obtained by biopsy. "Biopsy" in this case refers to a sample of skin cells or tissue taken for analysis. Several types of biopsy procedures are known and practiced in the field. The most common types include (1) incisional biopsy, in which only a sample of the tissue is taken; (2) excisional biopsy (or surgical biopsy), which consists of the total removal of a tumor mass, thus performing a therapeutic and diagnostic procedure; and (3) needle biopsy, in which a tissue sample is taken with a needle, which can be large or thin. Other types of biopsy exist, such as smears or curettage, and are also included in the present invention.

Alternatively, said skin cells can be obtained by stem cell differentiation (Guenou et al., *Lancet*, 374(9703): 1745-1753, 2009; Nissan et al., *Proc. Natl. Acad. Sci.*, 108(36): 14861-14866, 2011; Kraehenbuehl et al., *Nature Methods*, 8: 731-736, 2011). According to an embodiment, said stem cells are not human embryonic stem cells.

Skin cells according to the invention, whether they come from a biopsy or are obtained by differentiating stem cells, include at least one type of cell usually present in the hypodermis, dermis and/or epidermis. These cells include, among others, keratinocytes, melanocytes, fibroblasts, adipocytes, endothelial cells, mast cells, Langerhans cells and/or Merkel cells. Preferentially, the skin cells according to the invention include at least keratinocytes and/or fibroblasts. More preferentially, the skin cells according to the invention include keratinocytes and/or fibroblasts.

Many methods of skin cell culture are known to the skilled person. Any of these methods can be used to culture the skin cells of the invention. Advantageously, skin cells are cultured and/or stored under conditions that maintain, at least partially, cellular metabolism and/or cellular functions. The culture of skin cells according to the invention therefore includes both suspended skin cell cultures, monolayer skin cell cultures or bilayer skin cell cultures as well as tissue models, including reconstructed skin cultures and reconstructed mucosal cultures.

For example, suspended skin cell cultures have been routinely practiced in a very large number of laboratories for several decades. Similarly, single-layer or bilayer skin cell cultures have been known and used for a very long time.

In addition, many tissue models, including in particular reconstructed skin models and reconstructed mucosal models (Rosdy et al., *In Vitro Toxicol.*, 10(1): 39-47, 1997; Ponec et al., *J Invest Dermatol.*, 109(3): 348-355, 1997; Ponec et al., *Int J Pharm.*, 203(1-2): 211-225, 2000; Schmalz et al., *Eur J Oral Sci.*, 108(5): 442-448, 2000; Black et al., *Tissue Eng*, 11(5-6): 723-733, 2005; Dongari-Batgtzoglou et Kashleva, *Nat Protoc*, 1(4): 2012-2018, 2006; Bechtoille et al., *Tissue Eng*, 13(11): 2667-2679, 2007; Vrana et al., *Invest Ophthalmol Vis Sci*, 49(12): 5325-5331, 2008; Kinicoglu et al., *Biomaterials*, 30(32): 6418-6425, 2009; Auxenfans et al., *Eur J Dermatol*, 19(2): 107-113, 2009; Kinicoglu et al., *Biomaterials*, 32(25): 5756-5764, 2011; Costin et al., *Altern Lab Anim*, 39(4): 317-337, 2011; Auxenfans et al., *J Tissue Eng Regen Med*, 6(7): 512-518, 2012; Lequeux et al., *Skin Pharmacol Physiol*, 25(1): 47-55, 2012; EP 29 678; EP 285 471; EP 789 074; EP 1 451 302 B1; EP 1 878 790 B1; EP 1 974 718; US 2007/0148,771; US 2010/0,099,576; WO 02/070729; WO 2006/063864; WO 2006/0,63865; WO 2007/064305) are available to the skilled person and are included within the scope of the invention.

Advantageously, the tissue model includes reconstructed skin models and reconstructed mucosa models. Preferably, the reconstructed skin model is selected from the group consisting of dermal models, containing mainly stromal cells, and more particularly fibroblasts, epidermal models consisting mainly of keratinocytes, hypodermal models, skin models comprising a dermis and an epidermis, and skin models comprising a dermis, an epidermis and a hypodermis. Models comprising at least one dermis form connective tissue, while models comprising at least one epidermis form laminated epithelia comprising the characteristic layers of the tissue under consideration. For example, in epidermis models, a basal layer (*Stratum basalis*), a spiny layer (*Stratum spinosum*), a granular layer (*Stratum granulosum*), and a horny layer (*Stratum corneum*) can be identified. On the other hand, the reconstructed mucosa model according to the invention is a mucosa model of the mouth, gums, vagina or cornea.

Advantageously, said model is a connective tissue model of a dermis matrix comprising a matrix support preferably selected from:
  an inert support selected from the group consisting of a semipermeable synthetic membrane, in particular a semipermeable nitrocellulose membrane, a semipermeable nylon membrane, a Teflon membrane or sponge, a polycarbonate or polyethylene membrane, polypropylene, semi-permeable polyethylene terephthalate (PET), semi-permeable inorganic membrane, semi-permeable Anopore, acetate or cellulose ester (HATF) membrane, semi-permeable Biopore-CM membrane, semi-permeable polyester membrane, polyglycolic acid membrane or film.

This group includes, for example, the skin models Skin™ model ZK1100 and Dermagraft® and Transcyte® (Advanced Tissue Sciences);
  a treated plastic cell culture (formation of a dermal sheet: Michel et al., *In vitro Cell. Dev Biol.-Animal*, 35: 318-326, 1999);
  a gel or membrane based on hyaluronic acid (Hyalograft® 3D—Fidia Advanced Biopolymers) and/or collagen (such as an equivalent dermis or collagen lattices) and/or fibronectin and/or fibrin; this group includes for example the dermal model Vitrix® (Organogenesis);
  a porous matrix, surfaced or unsurfaced (for example a dermis equivalent), made from collagen which may contain one or more glycosaminoglycans and/or possibly chitosan (EP 0296078A1, WO 01/911821 and WO 01/92322).

This group includes, for example, the Mimederm® dermal model (BASF Beauty Care Solutions).

These matrix supports include stromal cells, particularly fibroblasts.

Advantageously, said skin model is an epidermis model comprising a matrix support preferably selected from:
  an inert support selected from the group consisting of a semipermeable synthetic membrane, in particular a semipermeable nitrocellulose membrane, a semipermeable nylon membrane, a Teflon membrane or sponge, a polycarbonate or polyethylene membrane, polypropylene, semi-permeable polyethylene terephthalate (PET), semi-permeable inorganic Anopore, acetate or cellulose ester (HATF) membrane, semi-permeable Biopore-CM membrane, semi-permeable polyester membrane;
  this group includes the reconstructed Epidermis models (Skinethic®) and the EpiDerm® model (Mattek Corporation);
  a film or membrane based on hyaluronic acid and/or collagen and/or fibronectin and/or fibrin.

Particular examples in this group include the models: Laserskin® (Fidia Advanced Biopolymers), Episkin® (L'Oréal).

These models can be inoculated with fibroblasts in the dermal part.

These models, in which fibroblasts may or may not be integrated, serve as a support for keratinocyte seeding and epidermal reconstitution. Advantageously, in addition to keratinocytes, pigment cells, immunocompetent cells, nerve cells are introduced; preferably immunocompetent cells are Langerhans cells.

Advantageously, said tissue model is a tissue model of reconstructed skin or mucosa comprising a dermal matrix or chorion support preferably selected from:
  an inert support selected from the group consisting of a semipermeable synthetic membrane, in particular a semipermeable nitrocellulose membrane, a semipermeable nylon membrane, a Teflon membrane or sponge, a polycarbonate or polyethylene membrane, polypropylene, of semi-permeable polyethylene terephthalate (PET), an inorganic membrane of semi-permeable Anopore, acetate or cellulose ester (HATF), a semi-permeable Biopore-CM membrane, a semi-permeable polyester membrane, said inert support containing or not stromal cells, in particular fibroblasts,
  a gel based on collagen and/or hyaluronic acid and/or fibronectin, and/or fibrin comprising stromal cells, in particular fibroblasts,
  a porous matrix, surfaced or unsurfaced, made from collagen which may contain one or more glycosaminoglycans and/or possibly chitosan, these porous matrices integrating stromal cells, in particular fibroblasts,
  a deepidermized or dead dermis, human or animal.

In this group, particular mention may be made of the models Mimeskin (BASF Beauty Care Solutions), EpidermFT™, EpiAirway™, EpiOccular™ EpiOral™, EpiGingival™, EpiVaginal™ (MatTek corporation), Human Corneal Epithelium (HCE), Human Oral Epithelium (HOE), Human Gingival Epithelium (HGE), Human Vaginal Epithelium (HVE) (Skinethic®), Phenion® Full Thickness Skin Model (Phenion) Apligraf® (Organogenesis), ATS-2000 (CellSystems® Biotechnologie Vertrieb) as well as Skin 2™ (ZK1200-1300-2000 Advanced Tissue Science).

There are also models dedicated to tissue therapy that can also be used in the context of the present invention. These include the Epidex (Modex Thérapeutiques), Epibase®

(Laboratoire Genévrier), Epicell™ (Genzyme), Autoderm™ and Transderm™ (Innogenetics).

The matrix support is then seeded with keratinocytes to reconstruct the epidermis and finally obtain a reconstructed skin.

Advantageously, the skin model used includes a model in which at least one complementary cell type has been incorporated, such as endothelial cells (EC) and/or immune cells such as lymphocytes, macrophages, mast cells, dendritic cells and/or fat cells and/or skin appendages, such as hair of the head and body, sebaceous glands.

The present invention also relates to a process for preparing the model of reconstructed sensitive skin as described above. The process for preparing the sensitive skin model of the invention comprises the steps of:
  a) obtaining a reconstructed skin model from a skin sample from a subject; and
  b) treating said reconstructed skin model from step a) with exogenous stress.

More particularly, the inventors have shown that the application of lactic acid makes it possible to obtain a model of reconstructed skin that reproduces the features of sensitive skin. In particular, the application of lactic acid leads to a greater expression of inflammation markers without compromising the histological structure of the skin or affecting skin cell viability. The exogenous stress of the invention will therefore preferably be an application of lactic acid.

According to this preferred embodiment, the process for preparing the model of the invention comprises the steps of:
  a) obtaining a reconstructed skin model from a skin sample from a subject; and
  b) contacting said reconstructed skin model from step a) with lactic acid.

Advantageously, said skin sample is as defined above.

Lactic acid can be used at any concentration to maintain the general structure of the skin while inducing the expression of inflammation markers. Preferably, the concentration of lactic acid used is between 0.05% and 5%, preferentially between 0.1% and 2.5%, more preferentially between 0.25% and 1.25%, notably between 0.4% and 0.8%. Lactic acid can be used in solution, at any concentration that maintains the general structure of the skin while inducing the expression of inflammation markers. Preferably, the concentration of lactic acid in the solution used should be between 0.05% and 5%, by weight of lactic acid/volume of solution. More preferably, lactic acid will be used at a concentration between 0.1% and 2.5%, even more preferably, at a concentration between 0.25% and 1.25%, even more preferably, at a concentration between 0.4% and 0.8%. According to the most preferred embodiment, lactic acid is used at a concentration of 0.6%, by weight of lactic acid/volume of solution.

According to an embodiment, said subject is an adult. In this case, the skin model of the invention is a model of adult skin. According to an embodiment, said subject is a child. In this case, the skin model of the invention is a model of child skin.

The model of reconstructed sensitive skin obtained by the process of the invention is as defined above. This model is particularly advantageous because it faithfully reproduces the features of sensitive skin as they emerge from the clinical study conducted by the inventors.

According to another preferred embodiment, the process of the invention comprises the steps of:
  a) obtaining a reconstructed skin model from a skin sample of a subject;
  b) contacting said reconstructed skin model from step a) with lactic acid; and
  c) measuring the expression level of at least one biological marker.

Advantageously, said biological marker is as defined above. Advantageously, the expression level of said biological marker is measured by the measurement methods as defined above.

According to a particular embodiment, step c) of the process of the invention includes measuring the expression level of at least one biological marker selected from the group of inflammation markers as defined above, barrier function markers as defined above and innate immunity and defense markers as defined above.

According to an embodiment, the process of the invention comprises the steps of:
  a) obtaining a reconstructed skin model from a skin sample of a subject;
  b) contacting said reconstructed skin model from step a) with lactic acid; and
  c) measuring the expression level of a combination of biological markers.

Said combination according to the invention comprises or consists of:
  at least one skin inflammation marker and at least one barrier marker as defined above; or
  at least one skin inflammation marker and at least one immune marker, as defined above; or
  at least one barrier marker and at least one immune marker, as defined above.

In a more preferential embodiment, said combination includes at least one skin inflammation marker and at least one barrier marker and at least one immune marker, as defined above.

The use of marker combinations comprising at least one marker of each of the different types indicated above is particularly advantageous.

In a particular embodiment, the process of the invention may comprise one or more intermediate steps between obtaining the reconstructed skin model and measuring the expression of the biological marker, said steps corresponding to the extraction from said reconstructed skin model of a lipid sample, an NMF sample, an mRNA (or the corresponding cDNA) sample or a protein sample. This can then be used directly to measure the expression of the marker. The preparation or extraction of mRNA (as well as its reverse-transcription into cDNA), proteins, lipids or NMFs from a sample of skin cells are routine procedures well known to the skilled person.

For some lipid markers such as prostaglandin E, it may not even be necessary to prepare a lipid sample. Indeed, this marker is secreted in the culture medium. It is then easy for the skilled person to determine the prostaglandin E2 from said culture medium. Several methods for the determination and quantification of prostaglandin E2 have thus been described in the art, including in particular ELISA methods. Such a method, to which the skilled person may refer, is thus detailed in the experimental part of the present application. It should also be noted that kits are commercially available for the determination of prostaglandin E2 (for example, at Cisbio Assays or Pierce).

According to an embodiment, the process of the invention further comprises a step d) of comparing the expression level of the biological marker in step c) with a reference expression level.

Advantageously, said reference expression level is as defined above. Advantageously, said comparison of the expression level of the biological marker in step c) with a reference expression level is as defined above.

The invention has the advantage of allowing the easy isolation and characterization of active ingredients, cosmetic raw materials and/or cosmetic formulations. This makes it easy to determine whether an active ingredient or formulation is effective in treating sensitive skin or whether it is well tolerated by sensitive skin. The sensitive skin model of the invention thus makes it possible to precisely determine which active ingredients have a beneficial effect on the prevention or treatment of sensitive skin. The processes of the invention are also suitable for evaluating the activity of formulations.

According to another aspect, the invention has as its object a method for evaluating the in vitro efficacy of an active ingredient or formulation to prevent or treat sensitive skin, said process comprising determining the level of expression and/or activation of at least one biological marker as defined above.

More precisely, the method of the invention preferentially comprises the following steps:
a) contacting said active ingredient or formulation with the sensitive skin model of the invention;
b) measuring the expression level of at least one biological marker of the invention in the skin model of step a); and
c) evaluating the effectiveness of said active ingredient or formulation according to the level in step b).

The "effectiveness of a formulation or active ingredient in preventing or treating sensitive skin" is defined in the present application as the ability of the formulation or active ingredient to cancel or reduce the effects associated with sensitive skin. Prevention in this case refers to treatment that is given before the effects of sensitive skin develop, while reduction refers to treatment that is given after the effects of sensitive skin have appeared.

The evaluation of step c) will be advantageous by comparing the expression level of step b) with a reference expression level. For example, the sensitive skin model that has not been treated by the active ingredient or formulation can be used as a control. In this case, the expression level of the biological marker of the invention is measured in said sensitive skin model before and after being contacted with the active ingredient or cosmetic formulation. The expression level of the biological marker of the invention can also be compared with that measured in normal skin.

The active ingredient or formulation is effective in preventing or treating sensitive skin if said active ingredient or formulation modulates the expression of the biological marker of the invention in such a way that after treatment it is more similar to that of said marker in normal skin. For example, an effective active or formulation results in a reduction in the expression of inflammation markers and/or an increase in the expression of barrier markers and/or an increase in the expression of defense markers and innate immunity compared to the untreated sensitive skin model.

The sensitive skin model of the invention also makes it easy to verify the tolerance, skin penetration and efficacy of an active ingredient or formulation. For example, it may be desirable, in some cases, to verify that these active ingredients or formulations are well tolerated and do not induce increased expression of markers indicating stress, such as inflammation-related markers.

The invention therefore also has as its object a process for evaluating the tolerance of an active ingredient or formulation, comprising the following steps:
a) contacting an active ingredient or formulation with a sensitive skin model;
b) measuring the expression level of at least one biological marker of the invention in the sensitive skin model; and
c) evaluating whether said active ingredient or formulation is well tolerated by sensitive skin.

The active ingredient is an active ingredient that is well tolerated by sensitive skin if said active ingredient does not modulate the expression of the biological marker of the invention. Similarly, the cosmetic formulation is well tolerated if the expression of the biological marker is not modulated by its addition to the sensitive skin model. That modulation may correspond, as the case may be, and in particular according to the nature of the biological marker, to an increase or decrease in the expression of said marker. Any of the markers identified here and described above can be used. In particular, the expression of inflammation markers is known to be increased when sensitive skin is attacked. On the other hand, the expression of these inflammation markers is not affected by well-tolerated active ingredients or formulations. In a preferred embodiment, the biological marker in step b) is a marker of inflammation. More preferably, the biological marker in step b) is IL1 or IL8.

The evaluation of step c) will be advantageous by comparing the expression level of step b) with a reference expression level. For example, the sensitive skin model that has not been treated by the active ingredient or formulation can be used as a control. In this case, the expression level of the biological marker of the invention is measured in said sensitive skin model before and after being contacted with the active ingredient or cosmetic formulation. The expression level of the biological marker of the invention can also be compared with that measured in normal skin.

The reference expression level is preferably the expression level of said biological marker in a skin model that has not been in contact with the active ingredient or formulation, allowing a meaningful comparison to be made between the expression level of step b) and said reference level. For example, the sensitive skin model that has not been treated by the active ingredient or formulation can be used as a control. In this case, the expression level of the biological marker of the invention is measured in said sensitive skin model before and after being brought into contact with the active agent or cosmetic formulation.

The process of the invention may further comprise a comparison of cell viability in the sensitive skin model treated with the active ingredient or formulation and in the control sample. In this case, the active ingredient or cosmetic formulation is well tolerated by sensitive skin if the cellular viability of the sample is not affected by the presence of the active ingredient or cosmetic formulation.

According to another preferred embodiment, the process of the invention therefore includes an additional step of determining cell viability in the sensitive skin model treated with the active ingredient or cosmetic formulation, determining cell viability in the control sample and comparing the two.

Many tests to determine cell viability are available to the skilled person and are commonly used in cosmetology. Of particular note is the MTT test, described for example in Mosman et al. (*J Immunol Methods,* 65(1-2): 55-63, 1983).

According to another aspect, the invention makes it possible to isolate formulations or active ingredients that reduce the effects of sensitive skin. In particular, the invention makes it possible to distinguish active ingredients or formulations according to their activity to treat the effects of sensitive skin. The invention is therefore particularly suitable for identifying formulations or active ingredients suitable for this very specific skin.

The invention therefore also relates to a process for identifying an active ingredient or formulation for the treatment of sensitive skin, characterized in that said process comprises the following steps:
- a) contacting said active ingredient or formulation with the sensitive skin model of the invention;
- b) measuring the expression level of at least one biological marker of the invention in the skin model of step a); and
- c) determining whether said active ingredient or formulation is suitable for treating sensitive skin according to the level in step b).

The candidate formulation is a formulation for the treatment of sensitive skin, if said candidate formulation allows the expression of at least one biological marker of the invention to be modulated. This modulation may correspond, according to the case, and in particular on the nature of the biological marker, to an increase or decrease in the expression of said marker. Similarly, the active candidate is an active for the treatment of sensitive skin, if said active candidate allows the expression of at least one biological marker of the invention to be modulated. This modulation may correspond, according to the case, and in particular on the nature of the biological marker, to an increase or decrease in the expression of said marker.

For example, it may be useful to isolate active ingredients or formulations that minimize the effects of sensitive skin on markers of defense and innate immunity, these formulations preserving the epidermis' ability to defend itself against attacks.

Similarly, it would be beneficial to identify active ingredients or formulations that minimize the effects of sensitive skin on barrier markers in order to maintain the integrity of the skin barrier. Finally, it may be desirable to isolate active ingredients or formulations that would not induce inflammation markers.

First, the formulation or active ingredient of interest is brought into contact with the sensitive skin model of the invention. This contact of the active ingredient of interest with the skin model can be done directly. Alternatively, it may be advantageous to formulate the active ingredient of interest, for example in such a way as to obtain a liquid composition, in order to facilitate its contact with the skin model. Thus, according to an embodiment of the invention, the process further comprises a step of formulating the active ingredient, in particular in the form of a liquid solution, in particular an aqueous solution, prior to the step of contacting said active ingredient with a skin model.

The invention will be described more precisely using the examples below.

FIGURES

FIG. 1: Hematoxylin/eosin staining of reconstructed epidermis.

Figure 2:
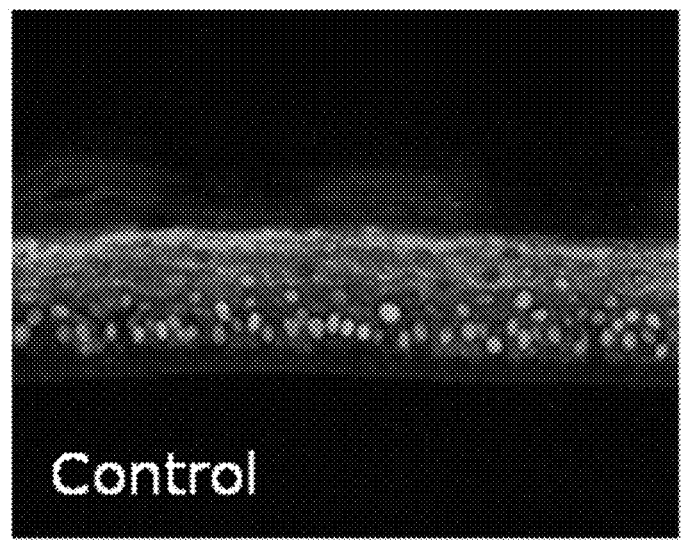
Figure 2:
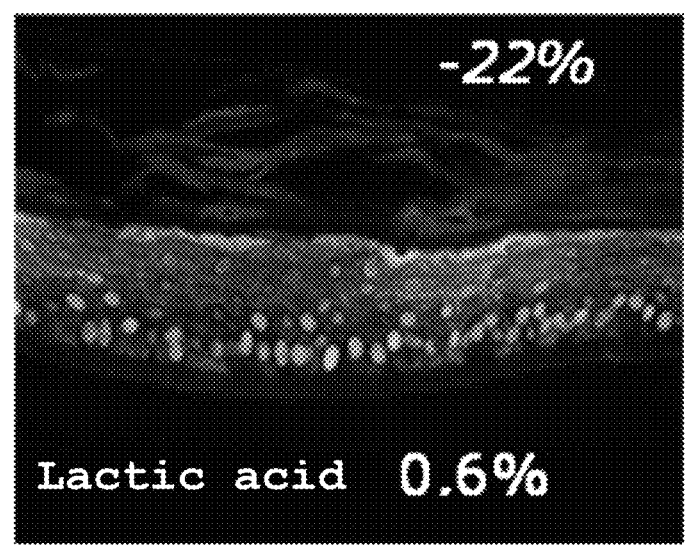

FIG. 2: Immunolabeling of involucrin (light gray) in reconstructed epidermis.

EXAMPLES

Example 1

Characterization of the Cellular, Molecular and Physiological Aspects of Sensitive Skin: Clinical Study A clinical study was evaluated on a panel of 97 subjects, including 77 children.

Subjects were interviewed using a questionnaire to classify them into two categories: sensitive skin or normal skin. The results of this ranking are described in Table 1.

TABLE 1

Ranking of the different subjects recruited for the clinical study, according to their age.

| Age group | Number of subjects (male/female) | |
|---|---|---|
| | Normal skin | Sensitive skin |
| 3-6 months | N = 15 (6/9) | N = 12 (8/4) |
| 6-12 months | N = 11 (5/6) | N = 11 (4/7) |
| 24-48 months | N = 18 (7/11) | N = 10 (6/4) |
| 18-20 years old | N = 10 (4/6) | N = 10 (4/6) |

A clinical evaluation was performed on different parts of each subject's face and body. The scaling, roughness, redness and cracks (SRRC) criteria and the overall dry skin score (ODS) criteria including the evaluation of skin dryness, were measured. This clinical evaluation showed that sensitive skin is generally more scaly, rougher and erythematous than normal skin.

Finally, this clinical evaluation and instrumental measurements were correlated with molecular analyses. Molecular analyses were performed on non-invasive biological samples for each subject (swab sampling):
- (i) Measurement of the levels cytokines IL1R1, IL1α and IL8;
- (ii) Measurement of the levels of polyunsaturated free fatty acids (arachidonic acid (C20:4 AA) and linoleic acid (C18:2 LA)).

Molecular analyses showed that the expression levels of inflammation markers such as cytokines and the levels of polyunsaturated free fatty acids (PUFA) are higher in sensitive skin than in normal skin, as expected.

Example 2

Development and Validation of a Model of Reconstructed Sensitive Skin

I. Materials and Methods a. Model Implemented—Induction of Lactic Acid Stress

Reconstructed human epidermises were obtained from the keratinocytes of a 19-year-old donor using the method derived from Poumay et al. (*Arch Dermatol Res* 2004; 296:203-11). After 2 days of immersion culture, the reconstructed human epidermises were cultured at the air/liquid interface for 10 days.

Epidermises at differentiation day 10 was treated topically with 0.6% lactic acid solution at 50 μL/epidermis and incubated for 48 hours, with re-treatment at 24 hours. At the end of the incubation, different parameters were measured to evaluate the effect of lactic acid on the reactivity of the epidermises.

b. Evaluation of the Viability of the Epidermises

The viability of the epidermises was assessed by an MTT metabolism test (n=2). The optical density (OD) at 540 nm is proportional to the amount of living cells and their metabolic activity.

c. Histological Analyses

The epidermises were mounted in paraffin (n=2), their morphology was evaluated following hematoxylin/eosin staining.

On the other hand, involucrin was stained by immunofluorescence (Alexa-488; green dye), the nuclei were stained by propidium iodide (red dye). The involucrin staining was quantified by measuring the fluorescence intensity reported on the surface of the living layers of the epidermis.

d. Gene Analyses

Gene expression of inflammatory markers and of markers of innate immunity and defense was evaluated by real-time quantitative PCR (qRT-PCR) on messenger RNAs extracted from epidermis (n=2). Gene expression of the innate immunity and defense markers, beta-defensin 2 hBD2, or Toll-like receptor 2, was also evaluated in the same way.

The gene expression analysis was performed in duplicate using a PCR array. The inflammatory marker genes studied are presented in Table 2.

The quantitative analysis of gene expression was based on the analysis of threshold cycles; relative expression (RE) was expressed in arbitrary units according to the following formula:

$$RE = (\frac{1}{2} \text{ number of cycles}) \times 10^6$$

TABLE 2

Classification of the genes studied

| Marker group | Gene | Abbreviation |
|---|---|---|
| Inflammation (tissue component) | Interleukin 1 alpha | IL1A |
| | Interleukin 1 beta | IL1B |
| | Interleukin 1 receptor antagonist | IL1RN |
| | Tumor Necrosis Factor | TNF |
| | Interleukin 8 | IL8 |
| | Prostaglandin-Endoperoxide Synthase 2 (=COX2) | PTGS2 |
| | Phospholipase A2, group IIF | PLA2G2F2F |
| Inflammation (vascular component): | Vascular Endothelial Growth Factor A | VEGF-A |
| | Thrombospondin 1 | THBS1 |
| Vascularization factors | Adenylate Cyclase Activating Polypeptide 1 (PACAP) | ADCYAP1 |
| Innate Immunity and Defense | Beta-Defensin-2 (hBD2) | DEFB4A |
| | Toll Like Receptor 2 | TLR2 | e. Determination of Inflammatory Markers
i. Determinations of Inflammatory Markers Released by the Epidermises The amount of inflammatory markers present in culture supernatants was assessed (n=6) using CBA kits (BD Biosciences) for IL-1 alpha (IL1α) and IL-8; and ELISA kits for VEGF (R&D Systems) and PGE2 (Enzo).

ii. Assessment of Intracellular Inflammatory Markers

Intracellular amounts of IL-1α, IL8 and IL1-RA were determined by ELISA (R&D Systems) in ground epidermis (n=2).

iii. Determination of Poly-Unsaturated Fatty Acids (PUFAs)

Screening of polyunsaturated fatty acids (PUFAs) expressed by the epidermis was carried out by GC/MS analysis of samples obtained after grinding the epidermises (n=2).

The amounts were normalized by C16:0 (palmitic acid), which is representative of the overall lipid content of the epidermis.

II. Results
a. Morphology and Viability of Reconstructed Epidermises

Lactic acid induced a moderate decrease in the viability of the epidermises (Table 3) and did not induce any major alteration in their morphology (FIG. 1).

TABLE 3

Viability of reconstructed epidermises (MTT)

| Reconstructed epidermises | Viability |
|---|---|
| Control | 100% |
| Lactic acid 0.6% | 66% | b. Evaluation of Lactic Acid-Modulated Gene Markers

The application of lactic acid to the surface of reconstructed epidermis induced stimulation of markers of inflammation of the tissue and vascular components, suggesting greater skin sensitivity (Table 4).

TABLE 4

Gene expression in reconstructed epidermises (qRT-PCR)

| Marker group | Genes | Control | Lactic acid 0.6% |
|---|---|---|---|
| Inflammation (tissue component) | IL1A | 100 | 240 |
| | IL1B | 100 | 195 |
| | IL1RN | 100 | 144 |
| | TNF | 100 | 105 |
| | IL8 | 100 | 649 |
| | PTGS2 | 100 | 182 |
| | PLA2G2F2F | 100 | 129 |
| Inflammation (vascular component): | VEGF-A | 100 | 138 |
| | THBS1 | 100 | 181 |
| Vascularization factors | ADCYAP1 | 100 | 117 |
| Innate immunity and defense | DEFB4A | 100 | 6 |
| | TLR2 | 100 | 54 |

Lactic acid treatment of reconstructed skins induced a decrease in the expression of innate immunity and defense markers (beta-defensin 2 hBD2-DEFB4A, Toll-like receptor 2 TLR2), suggesting an alteration in defense capabilities.

c. Expression of Involucrin

Lactic acid induced a decrease in the expression level of involucrin (−22%; FIG. 2), showing an alteration of the epidermal barrier.

d. Assessment of the Inflammatory Response

Lactic acid treatment induced an increase in the intracellular amount (Table 4) and the amount released into the supernatant (Table 5) of early markers of inflammation, such as inflammatory cytokines IL1-alpha (Interleukin 1-alpha, primary cytokine, main trigger of the inflammatory cascade) and IL8 (Interleukin 8, chemokine induced by de novo synthesis in stimulated keratinocyte).

At the intracellular level, the amount of IL1-RA (Interleukin 1 Receptor Antagonist, a member of the IL1 family that is induced in response to irritation, secondary to IL1) was also increased in response to lactic acid treatment, as was the IL1-RA/IL1-alpha ratio (Table 5).

The balance of the IL1-RA/IL1-alpha ratio allows skin homeostasis to be maintained. The increase in this ratio as well as the increase in IL1-RA are sensitive markers of the level of skin inflammation.

Lactic acid treatment induced induction of release of PGE2 (Prostaglandin E2, a lipid marker of the tissue component of inflammation) and VEGF (Vascular Endothelial Growth Factor, a vascular growth factor and marker of the vascular component of inflammation; Table 6).

TABLE 5

Intracellular determinations of inflammatory markers (ELISA)

| | Control | Lactic acid 0.6% | Change vs. control |
|---|---|---|---|
| IL8 (pg/mg protein) | 10.6 | 52.1 | +390% |
| IL1-alpha (pg/mg protein) | 88 | 794 | +806% |
| IL1-RA (pg/mg protein) | 2328 | 31243 | +1242% |
| IL1-RA/IL1-alpha ratio | 26.6 | 39.3 | +48% |

TABLE 6

Determinations of released inflammatory markers (ELISA)

| | Control | Lactic acid 0.6% | Change vs. control | |
|---|---|---|---|---|
| IL1-alpha (pg/ml) | 7 ± 1 | 23 ± 7 | +221% | ns |
| IL8 (pg/ml) | 65 ± 4 | 120 ± 18 | +84% | p < 0.05 |
| PGE2 (pg/ml) | 48 ± 4 | 149 ± 36 | +207% | p < 0.05 |
| VEGF (pg/ml) | 433 ± 17 | 1109 ± 45 | +156% | p < 0.001 | e. Poly-Unsaturated Fatty Acid (PUFA) Analysis

Screening of PUFAs reveals an inducing effect of lactic acid on proinflammatory omega-6 fatty acids involved in the arachidonic acid (AA) and linoleic acid (LA) pathways as well as proinflammatory omega-9 fatty acids involved in the oleic acid pathway (C18:1; Table 7).

TABLE 7

Determination of polyunsaturated fatty acids (PUFAs) in reconstructed epidermises (GC/MS); amounts normalized to C16:0

| PUFAs | Control | Lactic acid 0.6% | Change vs. control |
|---|---|---|---|
| C18:1 | 0.189 | 0.226 | +20% |
| C18:2 LA | 0.181 | 0.216 | +19% |
| C20:4 AA | 0.035 | 0.050 | +42% |

Conclusions

Treating the reconstructed skin models with lactic acid induced a significant increase in the expression of the different protein markers of the tissue and vascular components of inflammation, both at the transcript and protein level, as well as lipid markers of inflammation. This treatment of reconstructed skin models also induced a significant decrease in the expression of innate immunity and defense markers and barrier markers.

These data are correlated with the results obtained in the clinical study described in section 1 above.

The treatment of reconstructed skin models with lactic acid therefore makes it possible to reproduce the features of sensitive skin.

Example 3

Evaluation of the Effectiveness of Active Ingredients in the Reconstructed Sensitive Skin Model (Presented in Example 2)

I. Materials and Methods a. Compounds Evaluated—Dermocosmetic Active Ingredients The ingredients described below were evaluated in the reconstructed Sensitive Skin model obtained from Example 2 described above. The ingredients tested are cosmetic active ingredients with recognized anti-inflammatory properties.

Cycloceramide (OX100) [Laboratoires Expanscience]: tested at 10 and 100 µM

Cycloceramide is an active ingredient obtained by synthesis. It is a PKC inhibitor with anti-inflammatory properties (EP 2 266 530 B1; WO2006/11443 A1; WO 03/055463 A1; Piccardi et al., 2005, JID, vol 124, no. 4, suppl, abstract 216; Staquet et al., Int Arch Allergy Immunology, 2004, April; 133(4):348-56).

Peptide and sugar extract of Schizandra (SC) [Laboratoires Expanscience—trade name Sweetone®]: tested at 0.05% and 0.1%

This extract has anti-inflammatory and anti-redness properties demonstrated in vitro and clinically (WO2011/012612; WO2011/012615 A3; EP2015/077795; Brédif et al., 2013, JID, Volume 133, Issue S1, page S162, Abstract 953).

Dipotassium glycyrrhizinate (GLY) [Maruzen Pharmaceuticals]: tested at 0.005% and 0.01%

Dipotassium glycyrrhizinate is an extract of licorice with anti-inflammatory properties.

b. Protocol

Reconstructed human epidermises were obtained from the keratinocytes of a 2.5-month-old donor using the method derived from Poumay et al. (*Arch Dermatol Res* 2004; 296:203-11). After 2 days of immersion culture, the reconstructed human epidermises were cultured at the air/liquid interface for 10 days.

Epidermises at differentiation day 10 was treated or not (control) systemically with the test compounds and incubated for 24 hours. After incubation (day 11), treatment with 0.6% lactic acid (topical application of 50 µL/epidermis) was performed and the medium replaced by medium containing the test compounds and then the epidermises were incubated for 48 hours, with renewal of treatment at 24 hours (topical lactic acid and systemic test compounds).

At the end of incubation, the inflammatory parameters described below were measured to evaluate the effect of lactic acid on skin reactivity.

Determinations of inflammatory markers released by the epidermises (n=8)

The amount of inflammatory mediators IL-1alpha (IL1α), IL-8 and PGE2 present in skin culture supernatants was evaluated using ELISA kits (R&D Systems).

Evaluations of intracellular inflammatory markers IL-1α, IL8 and IL1-RA (n=2)

Same protocol as described in Example 2.

Determination of Poly-Unsaturated Fatty Acids (PUFAs) (n=2)

Same protocol as described in Example 2.

II. Results a. Assessment of the Inflammatory Response

The results confirm the observations described in Example 2 demonstrating the effect of lactic acid on the induction of an increase in intracellular (Table 8) and released (Table 9) amount of inflammation markers: IL8, IL1α, IL1RA, IL1RA/IL1α ratio, PGE2.

The active ingredients evaluated significantly inhibited these markers of inflammation:

Dipotassium Glycyrrhizinate (referred to as GLY in the results tables) significantly inhibited the increase in intracellular IL8, IL1α and IL1RA levels and the release of IL1α and PGE2 induced by lactic acid treatment. In addition, Dipotassium Glycyrrhizinate also maintained the IL1RA/IL1α ratio.

Peptide and sugar extract of Schizandra (SC) significantly inhibited the intracellular amount of IL1α and IL1RA, also preserving the balance of the IL1RA/IL1α ratio. Schizandra extract also inhibited the induction of PGE2 release.

Cycloceramide (OX100) significantly inhibited intracellular IL1RA increase and maintained the balance of the IL1RA/IL1α ratio. In addition, OX100 significantly inhibited the release of IL1α, IL8 and PGE2 induced by lactic acid.

TABLE 8

Intracellular measurements of inflammatory mediators (ELISA):
IL8, IL1α, IL1RA, IL1RA/IL1α ratio
In bold: Change vs. control; In italics: Change vs. lactic acid
Single-factor Analysis of Variance followed by Tukey test

| IL8 | IL8 Mean ± SD (pg/mg protein) | Change |
|---|---|---|
| Control | 37.23 ± 6.484 | |
| Lactic acid 0.6% | 79.20 ± 7.715 | +113% p < 0.01 |
| GLY 0.01% | 50.17 ± 3.366 | *−37% p < 0.05* |
| GLY 0.005% | 78.39 ± 6.350 | *−1% ns* |
| SC 0.1% | 53.00 ± 9.291 | *−33% ns* |
| SC 0.05%. | 70.57 ± 3.825 | *−11% ns* |

TABLE 8-continued

Intracellular measurements of inflammatory mediators (ELISA):
IL8, IL1α, IL1RA, IL1RA/IL1α ratio
In bold: Change vs. control; In italics: Change vs. lactic acid
Single-factor Analysis of Variance followed by Tukey test

| | | |
|---|---|---|
| OX100 100 μM | 56.95 ± 7.460 | *−28% ns* |
| OX100 10 μM | 76.24 ± 8.309 | *−4% ns* |

| IL1 alpha | IL1-alpha Mean ± SD (pg/mg protein) | Change |
|---|---|---|
| Control | 277.0 ± 46.67 | |
| Lactic acid 0.6% | 1044 ± 123.0 | +277% p < 0.001 |
| GLY 0.01% | 587.0 ± 63.64 | *−44% p < 0.01* |
| GLY 0.005% | 987.5 ± 101.1 | *−5% ns* |
| SC 0.1% | 448.0 ± 76.37 | *−57% p < 0.01* |
| SC 0.05% | 984.0 ± 116.0 | *−6% ns* |
| OX100 100 μM | 713.5 ± 113.8 | *−32% ns* |
| OX100 10 μM | 919.5 ± 53.03 | *−12% ns* |

| IL1RA | IL1RA Mean ± SD (pg/mg protein) | Change |
|---|---|---|
| Control | 5217 ± 688 | |
| Lactic acid 0.6% | 25750 ± 1974 | +394% p < 0.001 |
| GLY 0.01% | 11244 ± 1341 | *−56% p < 0.001* |
| GLY 0.005% | 25195 ± 1305 | *−2% ns* |
| SC 0.1% | 8605 ± 1527 | *−67% p < 0.001* |
| SC 0.05% | 22739 ± 1312 | *−12% ns* |
| OX100 100 μM | 14581 ± 1989 | *−43% p < 0.001* |
| OX100 10 μM | 23566 ± 1624 | *−8% ns* |

| IL1RA/IL1a ratio | IL1RA/IL1-alpha ratio Mean ± SD (pg/mg protein) | Change |
|---|---|---|
| Control | 18.93 ± 0.7142 | |
| Lactic acid 0.6% | 24.73 ± 1.011 | +31% p < 0.001 |
| GLY 0.01% | 19.14 ± 0.2121 | *−23% p < 0.001* |
| GLY 0.005% | 25.58 ± 1.287 | *+3% ns* |
| SC 0.1% | 19.20 ± 0.1556 | *−22% p < 0.001* |
| SC 0.05% | 23.20 ± 1.407 | *−6% ns* |
| OX100 100 μM | 20.46 ± 0.4808 | *−17% p < 0.001* |
| OX100 10 μM | 25.63 ± 0.2758 | *+4% ns* |

TABLE 9

Determinations of released inflammatory mediators (ELISA)

| | IL1-alpha | | IL8 | | PGE2 | |
|---|---|---|---|---|---|---|
| | Mean ± Standard deviation (pg/ml) | Change | Mean ± Standard deviation (pg/ml) | Change | Mean ± Standard deviation (pg/ml) | Change |
| Control | 11 ± 2 | | 78 ± 10 | | 29 ± 22 | |
| Lactic acid 0.6% | 68 ± 34 | +511% p < 0.001 | 209 ± 40 | +169% p < 0.001 | 197 ± 79 | +584% p < 0.001 |
| GLY 0.01% | 35 ± 16 | *−49% p < 0.05* | 244 ± 138 | *+17% ns* | 137 ± 83 | *−31% ns* |
| GLY 0.005% | 28 ± 10 | *−59% p < 0.01* | 211 ± 41 | *+1% ns* | 94 ± 36 | *−52% p < 0.05* |
| SC 0.1% | 91 ± 68 | *+34% ns* | 293 ± 49 | *+40% ns* | 127 ± 56 | *−36% ns* |
| SC 0.05% | 84 ± 59 | *+24% ns* | 261 ± 50 | *+25% ns* | 113 ± 39 | *−43% p < 0.05* |
| OX100 at 100 μM | 31 ± 19 | *−54% p < 0.05* | 146 ± 24 | *−30% p < 0.01* | 100 ± 48 | *−49% p < 0.01* |
| OX100 at 10 μM | 27 ± 13 | *−61% p < 0.01* | 175 ± 30 | *−16% ns* | 98 ± 28 | *−50% p < 0.01* |

In bold: Change vs. control;
In italics: Change vs. lactic acid Single-factor Analysis of Variance followed by Tukey test b. Poly-Unsaturated Fatty Acid (PUFA) Analysis The screening of PUFAs confirmed the inducing effect of lactic acid on proinflammatory omega-6 (C18:2; C20:4) and omega-9 (C18:1) fatty acids (Table 10).

The active ingredients evaluated showed an inhibitory effect of proinflammatory fatty acid induction.

TABLE 10

Determination of polyunsaturated fatty acids (PUFAs) in reconstructed epidermises (GC/MS); amounts normalized to C16:0

| | C18:1 | | C18:2 LA | | C20:4 AA | |
|---|---|---|---|---|---|---|
| | Mean ± SD | Change | Mean ± SD | Change | Mean ± SD | Change |
| Control | 0.1850 ± 0.02404 | | 0.09100 ± 0.01697 | | 0.0270 ± 0.008485 | |

TABLE 10-continued

Determination of polyunsaturated fatty acids (PUFAs) in reconstructed epidermises (GC/MS); amounts normalized to C16:0

|  | C18:1 | | C18:2 LA | | C20:4 AA | |
| --- | --- | --- | --- | --- | --- | --- |
|  | Mean ± SD | Change | Mean ± SD | Change | Mean ± SD | Change |
| Lactic acid 0.6% | 0.3880 ± 0.07212 | +110% p < 0.01 | 0.2130 ± 0.04808 | +134% p < 0.05 | 0.0575 ± 0.01626 | +113% ns |
| GLY 0.01% | 0.2680 ± 0.01697 | *−31%* *ns* | 0.1440 ± 0.01273 | *−32%* *ns* | 0.0395 ± 0.009192 | *−31%* *ns* |
| GLY 0.005% | 0.2785 ± 0.02475 | *−28%* *ns* | 0.1600 ± 0.01414 | *−25%* *ns* | 0.0435 ± 0.009192 | *−24%* *ns* |
| SC 0.1% | 0.2245 ± 0.01202 | *−42%* *p < 0.05* | 0.1190 ± 0.01273 | *−44%* *ns* | 0.0330 ± 0.002828 | *−43%* *ns* |
| SC 0.05% | 0.2520 ± 0.02404 | *−35%* *ns* | 0.1400 ± 0.01697 | *−34%* *ns* | 0.0350 ± 0.007071 | *−39%* *ns* |
| OX100 100 μM | 0.2065 ± 0.007778 | *−47%* *p < 0.05* | 0.0970 ± 0.008485 | *−54%* *p < 0.05* | 0.0265 ± 0.002121 | *−54%* *ns* |
| OX100 10 μM | 0.2795 ± 0.03323 | *−28%* *ns* | 0.1515 ± 0.02192 | *−29%* *ns* | 0.0380 ± 0.005657 | *−34%* *ns* |

In bold: Change vs. control;
In italics: Change vs. lactic acid Single-factor Analysis of Variance followed by Tukey test c. Conclusion In the model of sensitive skin on reconstructed epidermis, the active ingredients evaluated modulated the inflammatory response induced by lactic acid, by acting on the inflammatory mediators produced by skin cells (cytokines and prostaglandins) as well as on the inflammatory pathways derived from omega-6 and omega-9 fatty acids.

These results confirm the validity of the sensitive skin model. These results also confirm the validity of the sensitive skin model for use in methods for evaluating the effectiveness of cosmetic active ingredients in preventing or treating sensitive skin.

The invention claimed is:

1. A process for preparing a model of reconstructed sensitive skin, comprising the steps of:
   a) obtaining a skin sample from a subject;
   b) obtaining a reconstructed skin model from the skin sample of step a);
   c) contacting the reconstructed skin model from step b) with lactic acid for at least 48h, wherein the concentration of lactic acid used is about 0.6%; and
   d) measuring the expression level of a combination of biological markers, said combination comprising;
   skin inflammation markers comprising IL8, IL1α, ILR1A, ω-6 polyunsaturated fatty acids, ω-9 polyunsaturated fatty acids, prostaglandin E2, PLA2G2F, MGST1, and VEGF-A,
   barrier markers comprising involucrin, and
   defense markers comprising beta-defensin 2 and Toll-like receptor 2;
   wherein:
   (i) the expression level of the skin inflammation markers is higher in the reconstructed skin model from step d) than in normal skin; and
   (ii) the expression level of the barrier markers is lower in the reconstructed skin model from step d) than in normal skin; and
   (iii) the expression level of the defense markers is lower in the reconstructed skin model from step d) than in normal skin.

2. The process for preparing a model of reconstructed sensitive skin according to claim 1, wherein the concentration of lactic acid used is 0.6%.

3. The process for preparing a model of reconstructed sensitive skin according to claim 1, wherein said barrier markers further comprise, a ceramide selected from the group consisting of ceramides CER 1 to 9, and natural moisturizing factor (NMF).

4. The process for preparing a model of reconstructed skin according to claim 1, wherein said defense markers further comprise protein S100A7.

5. The process for preparing a model of reconstructed sensitive skin according to claim 1, wherein the reconstructed skin model of step b) is selected from the group consisting of suspended skin cell cultures, monolayer skin cell cultures, bilayer skin cell cultures, reconstructed skin cultures, and reconstructed mucosal cultures.

6. The process for preparing a model of reconstructed sensitive skin according to claim 1, wherein the skin sample of a subject from step a) comprises an explant of skin tissue or stem cells differentiated into skin cells.

7. The process for preparing a model of reconstructed sensitive skin according to claim 1, wherein said model of reconstructed skin from step b) comprises at least fibroblasts or keratinocytes.

* * * * *